(12) United States Patent
Stein et al.

(10) Patent No.: US 7,524,829 B2
(45) Date of Patent: Apr. 28, 2009

(54) ANTISENSE ANTIVIRAL COMPOUNDS AND METHODS FOR TREATING A FILOVIRUS INFECTION

(75

OTHER PUBLICATIONS

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.

Moulton, H. M., M. H. Nelson, et al. (2004). "Cellular uptake of antisense morpholino oligomers conjugated to arginine-rich peptides.", Bioconjug Chem., 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

O'Ryan, M. (1992). *Clinical Virology Manual*. S. Spector and G. Lancz. New York, Elsevier Science: 361-396.

Palu et al., *J. Biotech.*, 68:1-13 (1999).

Paul, A. V. (2002). Possible unifying mechanism of picornavirus genome replication. *Molecular Biology of Picornaviruses*. B. L. Semler and E. Wimmer. Washington, DC, ASM Press: 227-246.

Peters and LeDuc, *J. Infect. Dis.*, 179(Suppl. 1):ix-xvi (1999).

Sanchez et al., *Virsu Res.*, 29(3):215-240 (1993).

Summerton et al., *Biochim et. Biophys. ACTA*, 1489:141-158 (1999).

Summerton, J. and D. Weller (1997). "Morpholino antisense oligomers: design, preparation, and properties." *Antisense Nucleic Acid Drug Dev.*, 7(3): 187-95.

Summerton et al., *Antisense & Nucleic Acid Drug Development*, 7:63-70 (1997).

Toulme, J. J., R. L. Tinevez, et al. (1996). "Targeting RNA structures by antisense oligonucleotides." *Biochimie*, 78(7): 663-73.

Warfield et al., *J. Exp. Med.*, 200(2):169-179 (2004).

\* cited by examiner

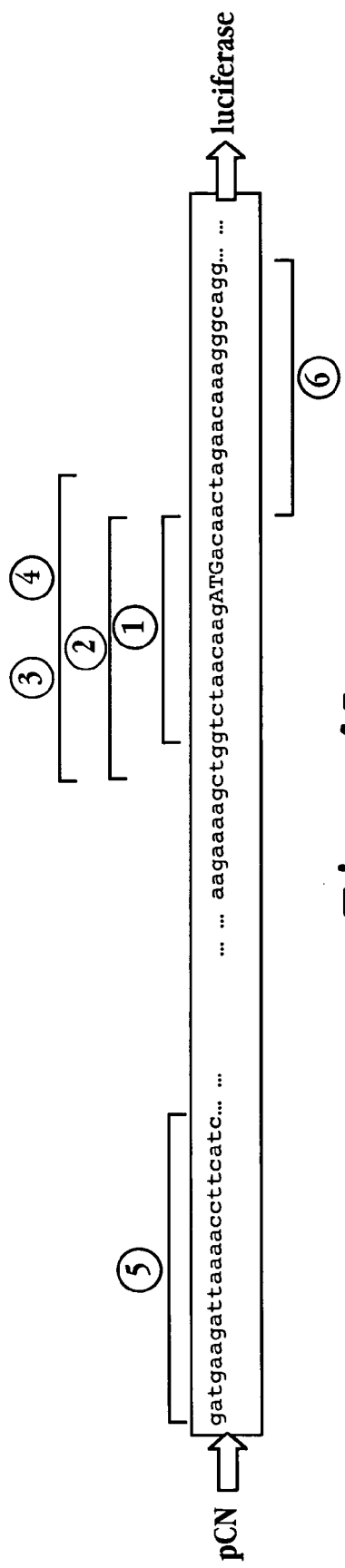

Inject Ebola

Monitor Mouse Survival

-24hrs  -4hrs  +24hrs

Fig. 9A

Fig. 9B days post challenge

-2 -1 -0 1 2 3 4 5 6 7 8 9

⟶ = SQ and IP tx (100-200 mg), bleed
⟶ = IM tx (12.5 mg)
On day 0, all five rhesus macaques were challenged with ~1000 pfu Ebola virus

Fig. 10

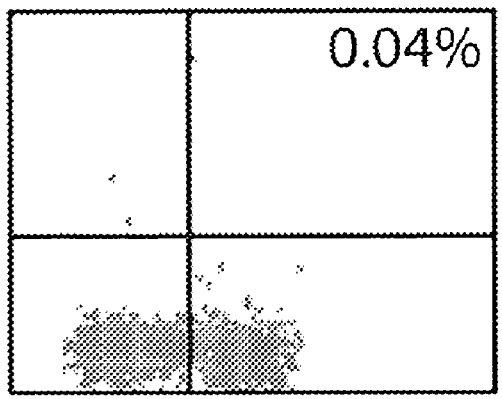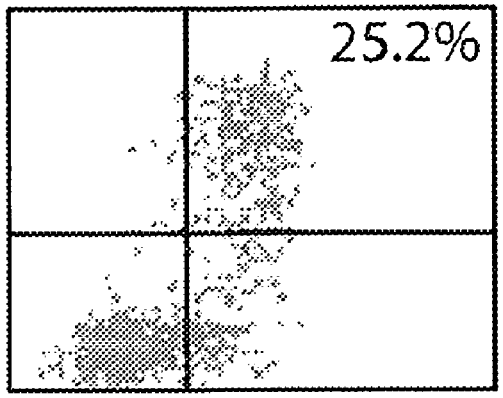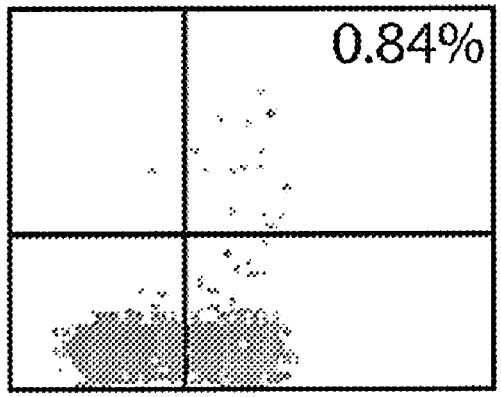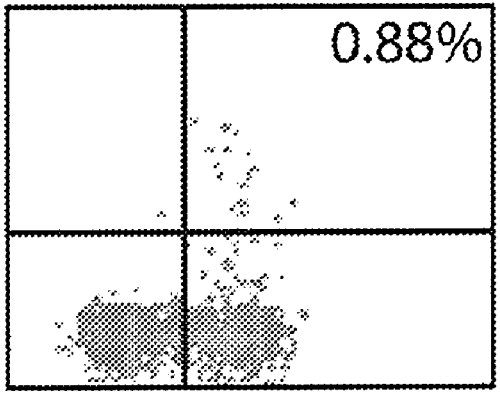
Fig. 14A

ANTISENSE ANTIVIRAL COMPOUNDS AND METHODS FOR TREATING A FILOVIRUS INFECTION

This application claims priority to U.S. provisional Patent Application No. 60/671,694 filed Apr. 14, 2005, and U.S. provisional Patent Application No. 60/624,277 filed Nov. 1, 2004, which are both incorporated herein in their entirety by reference.

FIELD OF THE INVENTION

This invention relates to antisense oligonucleotide compounds for use in treating an infection by a virus of the Filoviridae family and antiviral treatment methods employing the compounds. More specifically, it relates to treatment methods and compounds for treating viral infections in mammals including primates by Ebola and Marburg viruses.

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Arora, V. and P. L. Iversen (2001). "Redirection of drug metabolism using antisense technology." *Curr Opin Mol Ther* 3(3): 249-57.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Borio, L., T. Inglesby, et al. (2002). "Hemorrhagic fever viruses as biological weapons: medical and public health management." *Jama* 287(18): 2391-405.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Bray, M., K. Davis, et al. (1998). "A mouse model for evaluation of prophylaxis and therapy of Ebola hemorrhagic fever." *J Infect Dis* 178(3): 651-61.

Burnett, J., E. A. Henchal, et al. (2005). "The evolving field of biodefence: Therapeutic developments and diagnostics." *Nat Rev Drug Disc* 4: 281-297.

Connolly, B. M., K. E. Steele, et al. (1999). "Pathogenesis of experimental Ebola virus infection in guinea pigs." *J Infect Dis* 179 Suppl 1: S203-17.

Cross, C. W., J. S. Rice, et al. (1997). "Solution structure of an RNAxDNA hybrid duplex containing a 3'-thioformacetal linker and an RNA A-tract." *Biochemistry* 36(14): 4096-107.

Dagle, J. M., J. L. Littig, et al. (2000). "Targeted elimination of zygotic messages in Xenopus laevis embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'-->P5'phosphoramidate duplex forms an A-type helix in solution." *Nucleic Acids Res* 24(2): 354-60.

Egholm, M., O. Buchardt, et al. (1993). "PNA hybridizes to complementary oligonucleotides obeying the Watson-Crick hydrogen-bonding rules." *Nature* 365(6446): 566-8.

Feldmann, H., S. Jones, et al. (2003). "Ebola virus: from discovery to vaccine." *Nat Rev Immunol* 3(8): 677-85.

Feldmann, H. and M. P. Kiley (1999). "Classification, structure, and replication of filoviruses. " *Curr Top Microbiol Immunol* 235: 1-21.

Feldmann, H., H. D. Klenk, et al. (1993). "Molecular biology and evolution of filoviruses." *Arch Virol Suppl* 7: 81-100.

Felgner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Geisbert, T. W. and L. E. Hensley (2004). "Ebola virus: new insights into disease aetiopathology and possible therapeutic interventions." *Expert Rev Mol Med* 6(20): 1-24.

Geisbert, T. W., L. E. Hensley, et al. (2003). "Treatment of Ebola virus infection with a recombinant inhibitor of factor VIIa/tissue factor: a study in rhesus monkeys." *Lancet* 362(9400): 1953-8.

Jahrling, P. B., T. W. Geisbert, et al. (1999). "Evaluation of immune globulin and recombinant interferon-alpha2b for treatment of experimental Ebola virus infections." *J Infect Dis* 179 Suppl 1: S224-34.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl)carbonate, and 3'-(5-fluoro-2'-deoxyuridinyl) 5'-thymidinyl carbonate." *J Med Chem* 12(1): 154-7.

Moulton, H. M., M. H. Nelson, et al. (2004). "Cellular uptake of antisense morpholino oligomers conjugated to arginine-rich peptides." *Bioconjug Chem* 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

Peters, C. J. and J. W. LeDuc (1999). "An introduction to Ebola: the virus and the disease." *J Infect Dis* 179 Suppl 1: ix-xvi.

Sanchez, A., M. P. Kiley, et al. (1993). "Sequence analysis of the Ebolavirus genome: organization, genetic elements, and comparison with the genome of Marburg virus." *Virus Res* 29(3): 215-40.

Strauss, J. H. and E. G. Strauss (2002). *Viruses and Human Disease*. San Diego, Academic Press.

Summerton, J. and D. Weller (1997). "Morpholino antisense oligomers: design, preparation, and properties." *Antisense Nucleic Acid Drug Dev* 7(3): 187-95.

Toulme, J. J., R. L. Tinevez, et al. (1996). "Targeting RNA structures by antisense oligonucleotides." *Biochimie* 78(7): 663-73.

Warfield, K. L., J. G. Perkins, et al. (2004). "Role of natural killer cells in innate protection against lethal ebola virus infection." *J Exp Med* 200(2): 169-79.

BACKGROUND OF THE INVENTION

Minus-strand (−) RNA viruses are major causes of human suffering that cause epidemics of serious human illness. In humans the diseases caused by these viruses include influenza (Orthomyxoviridae), mumps, measles, upper and lower respiratory tract disease (Paramyxoviridae), rabies (Rhabdoviridae), hemorrhagic fever (Filoviridae, Bunyaviridae and Arenaviridae), encephalitis (Bunyaviridae) and neurological illness (Bornaviridae). Virtually the entire human population is thought to be infected by many of these viruses (e.g. respiratory syncytial virus) (Strauss and Strauss 2002).

The order Mononegavirales is composed of four minus strand RNA virus families, the Rhabdoviridae, the Paramyxoviridae, the Filoviridae and the Bornaviridae. The viruses in these families contain a single strand of non-segmented negative-sense RNA and are responsible for a wide range of significant diseases in fish, plants, and animals. Viruses with segmented (−) RNA genomes belong to the Arenaviridae, Bunyaviridae and Orthomyxoviridae families and possess genomes with two, three and seven or eight segments, respectively.

The expression of the five to ten genes encoded by the members of the Mononegavirales is controlled at the level of transcription by the order of the genes on the genome relative to the single 3' promoter. Gene order throughout the Mononegavirales is highly conserved. Genes encoding products required in stoichiometric amounts for replication are always at or near the 3' end of the genome while those whose products are needed in catalytic amounts are more promoter distal (Strauss and Strauss 2002). The segmented (−) RNA viruses encode genes with similar functions to those encoded by the Mononegavirales. Other features of virion structure and replication pathways are also shared among the (−) RNA viruses.

For some (−) RNA viruses, effective vaccines are available (e.g. influenza, mumps and measles virus) whereas for others there are no effective vaccines (e.g. Ebola virus and Marburg virus). In general, no effective antiviral therapies are available to treat an infection by any of these viruses. As with many other human viral pathogens, available treatment involves supportive measures such as anti-pyretics to control fever, fluids, antibiotics for secondary bacterial infections and respiratory support as necessary.

The development of a successful therapeutic for filoviruses Ebola and Marburg virus is a long-sought and seemingly difficult endeavor (Geisbert and Hensley 2004). Although they cause only a few hundred deaths worldwide each year, filoviruses are considered a significant world health threat and have many of the characteristics commonly associated with biological weapons since they can be grown in large quantities, can be fairly stable, are highly infectious as an aerosol, and are exceptionally deadly (Borio, Inglesby et al. 2002). Filoviruses are relatively simple viruses of 19 Kb genomes and consist of seven genes which encode nucleoprotein (NP), glycoprotein (GP), four smaller viral proteins (VP24, VP30, VP35 and VP40), and the RNA-dependent RNA polymerase (L protein) all in a single strand of negative-sensed RNA (Feldmann and Kiley 1999). The development of an effective therapeutic for Ebola virus has been hindered by a lack of reagents and a clear understanding of filovirus pathogenesis, disparity between animal models, and both the difficulty and danger of working with Ebola virus in biosafety level (BSL)-4 conditions (Geisbert and Hensley 2004; Burnett, Henchal et al. 2005). Administration of type I interferons, therapeutic vaccines, immune globulins, ribavirin, and other nucleoside analogues have been somewhat successful in rodent Ebola virus models, but not in infected nonhuman primates (Jahrling, Geisbert et al. 1999; Geisbert and Hensley 2004; Warfield, Perkins et al. 2004). Ebola virus frequently causes severe disseminated intravascular coagulation and administration of a recombinant clotting inhibitor has recently shown to protect 33% of rhesus monkeys (Geisbert, Hensley et al. 2003; Geisbert and Hensley 2004). Host-directed therapeutics alone have not proven to be a sufficiently efficacious therapeutic approach. A well-orchestrated sequence-specific attack on viral gene expression is required for a highly successful anti-filovirus therapeutic and treatment regimen.

In view of the severity of the diseases caused by (−) RNA viruses, in particular members of the Filoviridae family of viruses, and the lack of effective prevention or therapies, it is therefore an object of the present invention to provide therapeutic compounds and methods for treating a host infected with a (−) RNA virus.

SUMMARY OF THE INVENTION

The invention includes, in one aspect, an anti-viral antisense composition effective in inhibiting replication within a host cell of an Ebola virus or Marburg virus. The composition contains one or more antisense compounds that target viral RNA sequences within a region of the positive-strand mRNA that includes the region 5' and/or the 25-basepair region just downstream of the AUG start site of the (i) VP35 polymerase, (ii) the L polymerase, (iii) the VP24 membrane associated protein, (iv) the VP40 membrane-associated protein, and (v) the VP30 nucleoprotein. The antiviral compound(s) in the composition include an oligonucleotide analog having:

a) a nuclease-resistant backbone, b) 15-40 nucleotide bases, and c) a targeting sequence of at least 15 bases in length that hybridizes to a target region selected from the following:

i) the AUG start site region of VP35, as exemplified by antisense compounds SEQ ID NOs:21-26, ii) the AUG start site region of VP24, as exemplified by antisense compound SEQ ID NO:34, iii) the region 85 to 65 base pairs upstream of the AUG start site of VP24, as exemplified by SEQ ID NO:39, iv) the AUG start site region of polymerase L, as exemplified by antisense compound SEQ ID NO:17, and v) combinations of (i), (ii), (iii) and/or (iv).

The oligonucleotide analog also has:

a) the capability of being actively taken up by mammalian host cells, and b) the ability to form a heteroduplex structure with the viral target region, wherein said heteroduplex structure is:

i) composed of the positive or negative sense strand of the virus and the oligonucleotide compound, and ii) characterized by a Tm of dissociation of at least 45° C.

The compound may be composed of morpholino subunits linked by uncharged, phosphorus-containing intersubunit linkages, joining a morpholino nitrogen of one subunit to a 5' exocyclic carbon of an adjacent subunit. In one embodiment, the intersubunit linkages are phosphorodiamidate linkages, such as those having the structure:

$$Z=\overset{|}{\underset{|}{P}}-X$$
$$Y_1$$

[morpholine ring structure with O, N, and Pj]

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein X=$NR_2$, where each R is independently hydrogen or methyl. The compound may contain one or more cationic linkages wherein X=(1-piperazino).

The compound may also be a covalent conjugate of an oligonucleotide analog moiety capable of forming such a heteroduplex structure with the positive or negative sense strand of the virus, and an arginine-rich polypeptide effective to enhance the uptake of the compound into host cells. Exemplary polypeptides have one of the sequences identified as SEQ ID NOs:61-66.

Exemplary compositions include one or more antisense compounds that target a positive strand RNA region that includes:

(i) the AUG start site region of VP35, as exemplified by antisense compounds SEQ ID NOs:21-26, (ii) the AUG start site region of VP24, as exemplified by antisense compound SEQ ID NO:34, (iii) the region 85 to 65 base pairs upstream of the AUG start site of VP24, as exemplified by SEQ ID NO:39, (iv) the AUG start site region of polymerase L, as exemplified by antisense compound SEQ ID NO:17, and (v) combinations of (i) , (ii), (iii) and/or (iv).

The antisense compound(s) in the composition preferably target(s) at least 18, more preferably, at least 20 target base pairs.

In another aspect, the invention includes a method of treating an Ebola or Marburg virus infection in a mammalian host, by administering to the host, a therapeutically effective amount of a composition of the type described above. The method includes, in exemplary embodiments, administering a composition having a combination of antisense compounds targeted against different viral proteins, such as the VP35, VP24, and L polymerase proteins.

In a related, more general aspect, the invention includes a method of vaccinating a mammalian subject against Ebola or Marburg virus by pretreating the subject with the composition of the invention, and exposing the subject to the Ebola virus, preferably in an attenuated form.

These and other objects and features of the invention will become more fully apparent when the following detailed description of the invention is read in conjunction with the accompanying drawings.

BRIEF DESCRIPTION OF THE FIGURES

FIGS. 4A-4B show the target regions (SEQ ID NO:1 and SEQ ID NO:42) of 6 antisense compounds (SEQ ID NOS: 21, 22, 23, 24, 25, and 26) targeted against the VP35 gene in Ebola virus.

FIG. 7 is a plot of treatment efficacy, expressed as a fraction of mouse survivors 10 days post infection, as a function of VP35 antisense length.

FIG. 8 is a plot of treatment efficacy, expressed as percent survival, as a function of dose of various combinations of antisense compounds.

FIG. 9A shows the schedule of the experimental protocol. FIG. 9B plots the fraction of mouse survivors with various dose schedules of antisense compounds.

FIG. 10 is a schematic of the treatment schedule for a trial using PMO to treat Ebola infection in nonhuman primates.

FIG. 14 shows the immune responses of PMO-treated mice following survival of Ebola virus infection. (A) PMO-treated C57BL/6 mice that have previously survived EBOV infection generate EBOV-specific CD8+ responses. Pooled splenocytes from three PMO-treated EBOV survivors were re-stimulated in vitro with EBOV-specific VP35 or NP peptides, an irrelevant Lassa NP peptide as a negative control, or PMA/ionomycin as a positive control. The stimulated cells were stained after for 4 hours in culture with anti-CD44 FITC, anti-IFN-γ PE, and anti-CD8 Cy-Chrome. The percent of CD44+, IFN-γ+ cells among CD8+ lymphocytes is indicated in the upper right quadrant of each plot. These data are representative of the Ebola CD8 specific epitopes observed after challenge. (B) Total serum anti-Ebola virus antibodies were measured in surviving mice prior to or 4 weeks following treatment and challenge. PMO mice were treated with the combination of PMOs 24 and 4 hours before challenge and their antibody responses are compared with mice treated with Ebola VLPs 24 hours before EBOV infection. The results are depicted as the endpoint titers of the individual mice (circles). The horizontal line in each column represents the geometric mean titer of the group. (C) Mice that previously survived EBOV challenge following PMO treatment were re-challenged with 1000 pfu of mouse-adapted Ebola virus 4 weeks after the initial challenge. Results are plotted as percent survival for the PMO-treated mice (black) and naive control mice (n=10 per group).

DETAILED DESCRIPTION OF THE INVENTION

I. Definitions

The terms below, as used herein, have the following meanings, unless otherwise indicated:

The terms "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 1A-1D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166, 315, 5,521,063, and 5,506,337, all of which are incorporated herein by reference.

Figure 1A:
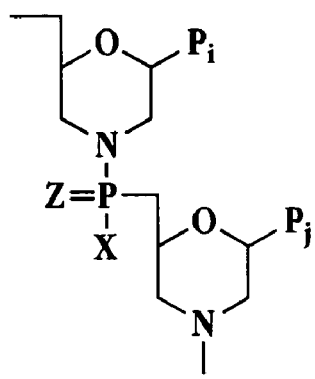
FIGS. 1A-1D show the repeating subunit segment of several preferred morpholino oligonucleotides, designated A through D, constructed using subunits having 5-atom (A), six-atom (B) and seven-atom (C-D) linking groups suitable for forming polymers.
Figure 1B:
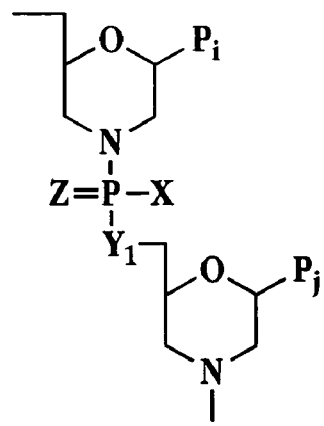

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 1B, where X=$NH_2$, NHR, or $NR_2$ (where R is lower alkyl, preferably methyl), Y=O, and Z=O, and $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 1B, X=lower alkoxy, such as methoxy or ethoxy, Y=NH or NR, where R is lower alkyl, and Z=O. A cationic linkage can be introduced into the backbone by utilizing X=(1-piperazino) as shown in FIG. 1B.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to at least one of the following: 1) a 125 nucleotide region that surrounds the AUG start codon of a viral messenger RNA and/or; 2) the terminal 30 bases of the 3' terminal end of the minus-strand viral RNA (e.g. virion RNA or vRNA) and/or; 3) the terminal 25 bases of viral mRNA transcripts The term "target sequence" refers to a portion of the target RNA against which the oligonucleotide analog is directed, that is, the sequence to which the oligonucleotide analog will hybridize by Watson-Crick base pairing of a complementary sequence. As will be seen, the target sequence may be a contiguous region of the viral positive-strand mRNA or the minus-strand vRNA.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. For example, as will be seen, the target and targeting sequences are selected such that binding of the analog to a portion of a 125 nucleotide region associated with the AUG start codon of the positive-sense RNA strand (i.e., mRNA) of the virus acts to disrupt translation of the viral gene and reduce viral replication.

The term "AUG start site region" includes a 125 nucleotide region in both the 5' and 3' direction relative to the AUG start codon of viral mRNAs. The region includes about 25 nucleotides downstream (i.e., in a 3' direction) and 100 nucleotides upstream (i.e., in a 5' direction) as exemplified by the targets sequences shown as SEQ ID NOs: 1-6 for Ebola virus and SEQ ID NOs: 8-13 for Marburg virus.

Target and targeting sequences are described as "complementary" to one another when hybridization occurs in an antiparallel configuration. A targeting sequence may have "near" or "substantial" complementarity to the target sequence and still function for the purpose of the present invention, that is, still be “complementary.” Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog “specifically hybridizes” to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with “near” or “substantial” complementary of the antisense oligomer to the target sequence, as well as with exact complementarity.

A “nuclease-resistant” oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A “heteroduplex” refers to a duplex between an oligonculeotide analog and the complementary portion of a target RNA. A “nuclease-resistant heteroduplex” refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A “base-specific intracellular binding event involving a target RNA” refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An “effective amount” of an antisense oligomer, targeted against an infecting filovirus, is an amount effective to reduce the rate of replication of the infecting virus, and/or viral load, and/or symptoms associated with the viral infection.

As used herein, the term “body fluid” encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term “relative amount” is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

“Treatment” of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term “improved therapeutic outcome” relative to a patient diagnosed as infected with a particular virus, refers to a slowing or diminution in the growth of virus, or viral load, or detectable symptoms associated with infection by that particular virus.

An agent is “actively taken up by mammalian cells” when the agent can enter the cell by a mechanism other than passive diffusion across the cell membrane. The agent may be transported, for example, by “active transport”, referring to transport of agents across a mammalian cell membrane by e.g. an ATP-dependent transport mechanism, or by “facilitated transport”, referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, or polyarginine, to facilitate transport into the target host cell as described (Moulton, Nelson et al. 2004). The compound may also have one or more cationic linkages to enhance antisense activity and/or cellular uptake. A preferred cationic linkage is shown in FIG. 1B where X=(1-piperazino).

The term "filovirus" refers collectively to members of the Filoviridae family of single stranded (−) RNA viruses including Ebola and Marburg viruses listed in Table 1 below.

II. Targeted Viruses

The present invention is based on the discovery that effective inhibition of single-stranded, negative-sense RNA ((−)RNA)viruses can be achieved by exposing cells infected with the virus to antisense oligonucleotide analog compounds (i) targeted against the AUG start codon of the positive sense viral mRNAs or the 3' termini of the negative strand viral RNA, and (ii) having physical and pharmacokinetic features which allow effective interaction between the antisense compound and the virus within host cells. In one aspect, the oligomers can be used in treating a mammalian subject infected with the virus.

The invention targets RNA viruses having genomes that are: (i) single stranded, (ii) negative polarity, and (iii) less than 20 kb. The targeted viruses also synthesize a RNA species with positive polarity, the positive-strand or sense RNA, as the requisite step in viral gene expression. In particular, targeted viruses include those of the Filoviridae family referred to herein as filoviruses. Targeted viruses organized by family, genus and species are listed in Table 1. Various physical, morphological, and biological characteristics of each of the Filoviridae family, and members therein, can be found, for example, in Textbook of Human Virology, R. Belshe, ed., *2nd Edition*, Mosby, 1991, in "Viruses and Human Disease" (Strauss and Strauss 2002) and at the Universal Virus Database of the International Committee on Taxonomy of Viruses (world wide web ncbi.nlm.nih.gov/ICTVdb/index.htm). Some of the key biological characteristics of each family are summarized below following Table 1.

TABLE 1

Targeted viruses of the invention organized by family and genus

| Family | Genus | Virus |
|---|---|---|
| Filoviridae | Marburg-like | Marburg virus (MARV) |
| | Ebola-like | Zaire Ebola virus (ZEBOV) |
| | | Sudan Ebola virus (SEBOV) |
| | | Reston Ebola virus (REBOV) |
| | | Cote d'Ivoire Ebola (ICEBOV) |

A. Filoviridae

The Filoviridae family is composed of two members, Ebola virus (EBOV) and Marburg virus (MARV). Four species of Ebola have been identified to date and are named by the location of where they were identified including Ebola Ivory Coast (ICEBOV), Ebola Zaire (ZEBOV), Ebola Sudan (SEBOV) and Ebola Reston (REBOV). Ebola Reston is the only known filovirus that does not cause severe human disease. The filovirus structure is pleomorphic with shapes varying from long filaments to shorter contorted structures. The viral filaments measure up to 14,000 nm in length and have uniform diameter of 80 nm. The virus filament is envelope in a lipid membrane. The virion contains one, single-stranded, negative sense RNA.

The first filovirus was recognized in 1967 after laboratory workers in Marburg Germany developed hemorrhagic fever following studies involving handling tissues from green monkeys. The Marburg outbreak led to 31 cases and seven deaths. The first Ebola virus was identified in 1976 following outbreaks of Ebola hemorrhagic fever in northern Zaire (now the Democratic Republic of Congo) and southern Sudan. Eventually, two distinct viral isolates were recognized. Ebola Zaire was lethal in 90% of the infected cases and Ebola Sudan was lethal in 50% of the cases. A list of Ebola hemorrhagic fever case is compiled for Ebola Zaire in TABLE 2.

TABLE 2

Chronological order of Ebola Zaire Outbreaks

| Date | Location | Human Cases | Deaths |
|---|---|---|---|
| 1976 | Zaire | 318 | 280 (88%) |
| 1977 | Zaire | 1 | 1 (100%) |
| 1994 | Gabon | 49 | 29 (59%) |
| 1995 | Dem. Rep. Congo | 315 | 255 (81%) |
| 1996 | Gabon | 31 | 21 (68%) |
| 1996 | Gabon | 60 | 45 (75%) |
| 1996 | South Africa | 2 | 1 (50%) |
| 2001 | Gabon and Congo | 122 | 96 (79%) |

The summary of these outbreak data include 899 cases resulting in 728 deaths or an overall 81% rate of lethality observed over a period of 25 years. A single case of Ebola Ivory Coast was reported in 1994 and that infection was not lethal. Finally, 4 outbreaks of Ebola Sudan from 1976 to 2001 produced 744 cases resulting in 398 deaths or an overall rate of lethality of 53%. These observations indicate Ebola Zaire is the virus of greatest concern both in apparent prevalence and lethality. It appears Ebola is transmitted to humans from ongoing life cycles in animals other than humans which make it a zoonotic virus. Ebola can replicate in various rodents such as mice, guinea pigs and some species of bats. Some types of bats are native to areas where the virus is found which suggests the bat may be the natural host and viral reservoir. Once a human is infected, person-to-person transmission is the means for further infections. During recorded outbreaks, individuals that cared for or worked closely with infected people were at high risk of becoming infected. Nosocomial transmission has also been an important factor in the spread of viral infection during outbreaks. In the laboratory setting, viral spread through small-particle aerosols has been clearly demonstrated.

The incubation period for Ebola hemorrhagic fever ranges from 2 to 21 days. The clinical symptoms include abrupt onset of fever, headache, joint and muscle aches, sore throat and weakness. These symptoms are then followed by diarrhea, vomiting and stomach pain which do not help in diagnosis of infection. Diagnosis is suspected when this group of symptoms is observed in an area where Ebola is known to be active. Patients who die usually have not developed a significant immune response to the virus at the time of death. There are no known treatments for filovirus infections.

Figure 3A:
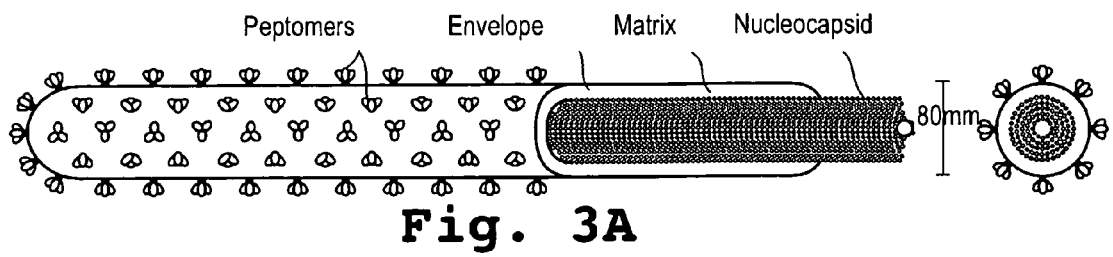
FIGS. 3A-3C illustrate the components and morphology of a filovirus (3A), and show the arrangement of viral genes in the Ebola virus (Zaire) (3B), and the Marburg virus (3C).
Figure 3B:
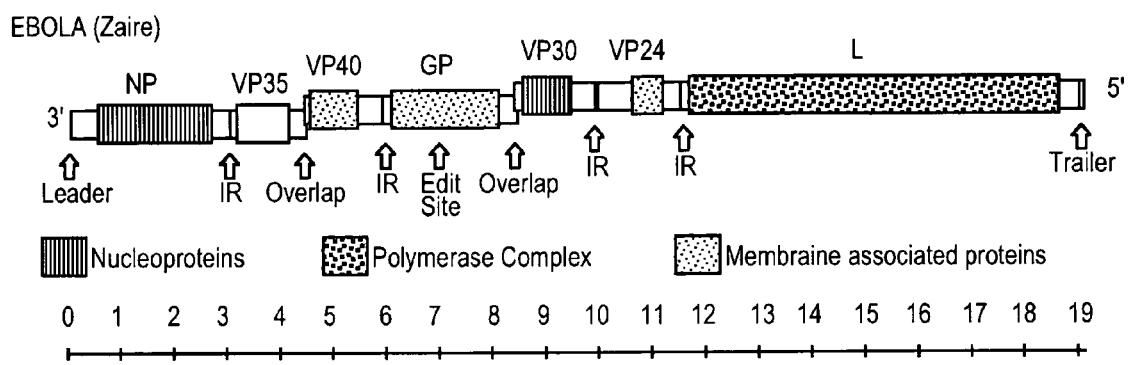
Figure 3C:
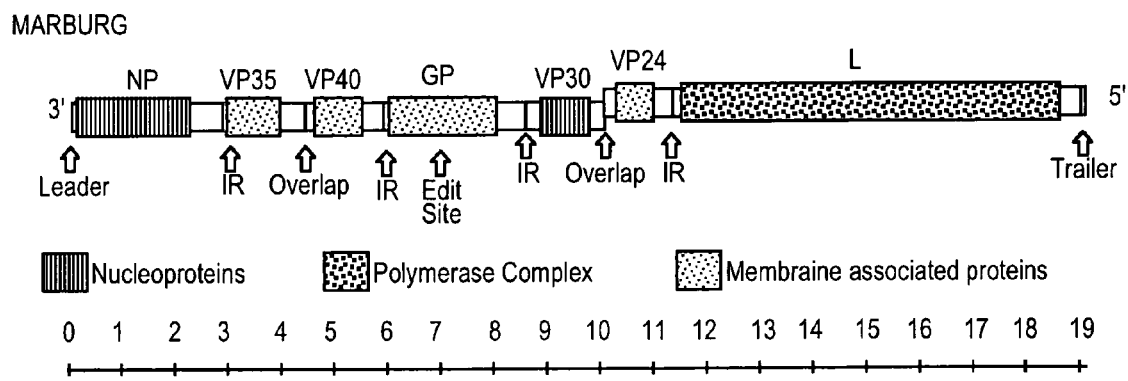

The filovirus virus genome is approximately 19,000 bases of single-stranded RNA that is unsegmented and in the antisense (i.e. negative sense) orientation. The genome encodes 7 proteins from monocistronic mRNAs complementary to the vRNA as shown in FIG. 3. A review of filoviruses can be found in Fields Virology and (Strauss and Strauss 2002).

Ebola Virus

Ebola virus (EBOV), a member of the family Filoviridae and the order Mononegavirales, is an enveloped, nonsegmented negative-strand RNA virus and is one of the most lethal human and nonhuman primate pathogens recognized to date. Four subtypes of Ebola virus have been identified, including Zaire (ZEBOV), Sudan (SEBOV), Ivory Coast (ICEBOV), and Reston (REBOV) (Sanchez, Kiley et al. 1993). Human infection with subtype Zaire causes a fulminating, febrile, hemorrhagic disease resulting in extensive mortality (Feldmann, Klenk et al. 1993; Peters and LeDuc 1999; Feldmann, Jones et al. 2003).

Ebola virus particles have a filamentous appearance, but their shape may be branched, circular, U- or 6-shaped, or long and straight. Virions show a uniform diameter of approximately 80 nm, but vary greatly in length. Ebola virus particles consist of seven structural proteins. The glycoprotein (GP) of Ebola virus forms spikes of approximately 7 nm, which are spaced at 5- to 10-nm intervals on the virion surface.

Marburg Virus

Marburg virus (MARV) was first recognized in 1967, when an outbreak of hemorrhagic fever in humans occurred in Germany and Yugoslavia, after the importation of infected monkeys from Uganda. Thirty-one cases of MARV hemorrhagic fever were identified that resulted in seven deaths. The filamentous morphology of the virus was later recognized to be characteristic, not only of additional MARV isolates, but also of EBOV. MARV and EBOV are now known to be distinctly different lineages in the family Filoviridae, within the viral order Mononegavirales (Strauss and Strauss 2002).

Few natural outbreaks of MARV disease have been recognized, and all proved self-limiting, with no more than two cycles of human-to-human transmission. However, the actual risks posed by MARV to global health cannot be assessed because factors which restrict the virus to its unidentified ecological niche in eastern Africa, and those that limit its transmissibility, remain unknown. Concern about MARV is further heightened by its known stability and infectivity in aerosol form. A recent (2005) epidemic in eastern Africa caused at least 200 deaths and further increases the concern about MARV.

B. Target Sequences

The filovirus structure is pleomorphic with shapes varying from long filaments to shorter contorted structures. The viral filaments measure up to 14,000 nm in length and have uniform diameter of 80 nm. The virus filament is envelope in a lipid membrane. The virion contains one, single-stranded, negative sense RNA. The filovirus virus genome is approximately 19,000 bases of single-stranded RNA that is unsegmented and in the antisense orientation. The genome encodes 7 proteins from monocistronic mRNAs complementary to the vRNA. A diagram of a representative filovirus and its genome is provided in FIGS. 3A-3C (taken from Fields Virology).

The targets selected were positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and L, nucleoproteins NP and VP30, and membrane-associated proteins VP24 and VP40. Among these early proteins are favored, e.g., VP35 is favored over the later expressed L polymerase. As will be seen, a preferred single-compound target is VP35 that spans the AUG start site, and/or targets a region within 100 bases upstream or 25 bases downstream of the translational start site. Preferred combinations of targets include the VP35-AUG target plus the VP24-AUG start site (or the 100-base region upstream or 25-base-region downstream of the start site) and or the L polymerase AUG start site (or the 100-base region upstream or 25-base-region downstream of the start site).

Additional targets include the terminal 25 base pair region of the viral mRNA transcripts as represented by the sequences complementary to the SEQ ID NOs:42 and 43. These targets are preferred because of their high degree of sequence conservation across individual filovirus isolates.

The Ebola virus RNA sequences (Zaire Ebola virus, Mayinga strain) can be obtained from GenBank Accession No. AF086833. The particular targeting sequences shown below were selected for specificity against the Ebola Zaire virus strain. Corresponding sequences for Ebola Ivory Coast, Ebola Sudan and Ebola Reston (GenBank Acc. No. AF522874) are readily determined from the known GenBank entries for these viruses. Preferably targeting sequences are selected that give a maximum consensus among the viral strains, particularly the Zaire, Ivory Coast, and Sudan strains, or base mismatches that can be accommodated by ambiguous bases in the antisense sequence, according to well-known base pairing rules.

GenBank references for exemplary viral nucleic acid sequences representing filovirus genomic segments are listed in Table 3 below. The nucleotide sequence numbers in Table 3 are derived from the GenBank reference for the positive-strand RNA of Ebola Zaire (AF086833) and Marburg virus (229337). It will be appreciated that these sequences are only illustrative of other sequences in the Filoviridae family, as may be available from available gene-sequence databases of literature or patent resources (See e.g. world wide web ncbi.nlm.nih.gov). The sequences in Table 3 below, identified as SEQ ID NOS: 1-14, are also listed in the Sequence Listing table at the end of the specification.

The target sequences in Table 3 represent the 3' terminal 30 bases of the negative sense viral RNA or the 125 bases surrounding the AUG start codons of the indicated filovirus genes. The sequences shown are the positive-strand (i.e., antigenomic or mRNA) sequence in the 5' to 3' orientation. It will be obvious that when the target is the minus-strand vRNA, as in the case of the Str Inh 1 target (SEQ ID NOs: 15 and 44) the targeted sequence is the complement of the sequence listed in Table 3.

Table 3 lists the targets for exemplary Ebola viral genes VP35, VP24, VP30, VP40, L and NP. The proteins represent six of the seven proteins encoded by Ebola. The target sequences for the AUG start codons of the six genes are represented as SEQ ID NOs:1-6. The corresponding set of target sequences for Marburg virus are shown as SEQ ID NOs:8-13. The 3' terminal sequence of the minus-strand viral RNA (SEQ ID NOs:7 and 14) can also be targeted. The sequences shown in Table 3 for the 3' terminal minus-strand targets (SEQ ID NOs:7 and 14) are the minus-strand sequences in a 5'-3' orientation for Ebola and Marburg viruses, respectively.

TABLE 3

Exemplary Filovirus Nucleic Acid Target Sequences

| Name | GenBank No. | Nucleotide Region | Sequence (5' to 3') | SEQ ID NO |
|---|---|---|---|---|
| VP35-AUG | AF086833 | 3029-3153 | AAUGAUGAAGAUUAAAACCUUCAUCA UCCUUACGUCAAUUGAAUUCUCUAGC ACUCGAAGCUUAUUGUCUUCAAUGUA AAAGAAAAGCUGGUCUAACAAGAUGA CAACUAGAACAAAGGGCAGGG | 1 |
| VP24-AUG | AF086833 | 10245-10369 | CGUUCCAACAAUCGAGCGCAAGGUUU CAAGGUUGAACUGAGAGUGUCUAGAC AACAAAAUAUUGAUACUCCAGACACC | 2 |

TABLE 3-continued

Exemplary Filovirus Nucleic Acid Target Sequences

| Name | GenBank No. | Nucleotide Region | Sequence (5' to 3') | SEQ ID NO |
|---|---|---|---|---|
| | | | AAGCAAGACCUGAGAAAAAACCAUGG CUAAAGCUACGGGACGAUACA | |
| VP30-AUG | AF086833 | 8409-8533 | AGAUCUGCGAACCGGUAGAGUUUAGU UGCAACCUAACACACAUAAAGCAUUG GUCAAAAAGUCAAUAGAAAUUUAAAC AGUGAGUGGAGACAACUUUUAAAUGG AAGCUUCAUAUGAGAGAGGAC | 3 |
| VP40-AUG | AF086833 | 4379-4503 | AAACCAAAAGUGAUGAAGAUUAAGAA AAACCUACCUCGGCUGAGAGAGUGUU UUUUCAUUAACCUUCAUCUUGUAAAC GUUGAGCAAAAUUGUUAAAAAUAUGA GGCGGGUUAUAUUGCCUACUG | 4 |
| L-AUG | AF086833 | 11481-11605 | GUAGAUUAAGAAAAAAGCCUGAGGAA GAUUAAGAAAAACUGCUUAUUGGGUC UUUCCGUGUUUUAGAUGAAGCAGUUG AAAUUCUUCCUCUUGAUAUUAAAUGG CUACACAACAUACCCAAUAC | 5 |
| NP-AUG | AF086833 | 370-494 | UGAACACUUAGGGGAUUGAAGAUUCA ACAACCCUAAAGCUUGGGGUAAAACA UUGGAAAUAGUUAAAAGACAAAUUGC UCGGAAUCACAAAAUUCCGAGUAUGG AUUCUCGUCCUCAGAAAAUCU | 6 |
| Str. Ihn 1(-) | AF086833 | 30-1 | UAAAAAUUCUUCUUUCUUUUUGUGUG UCCG | 7 |
| VP35-AUG | Z29337 | 2844-2968 | CUAAAAAUCGAAGAAUAUUAAAGGUU UUCUUUAAUAUUCAGAAAAGGUUUUU UAUUCUCUUCUUUCUUUUUGCAAACA UAUUGAAAUAAUAAUUUUCACAAUGU GGGACUCAUCAUAUAUGCAAC | 8 |
| VP24-AUG | Z29337 | 10105-10229 | UUCAUUCAAACACCCCAAAUUUUCAA UCAUACACAUAAUAACCAUUUUAGUA GCGUUACCUUUCAAUACAAUCUAGGU GAUUGUGAAAAGACUUCCAAACAUGG CAGAAUUAUCAACGCGUUACA | 9 |
| VP30-AUG | Z29337 | 8767-8891 | GAAGAACAUUAAGUGUUCUUUGUUAG AAUUAUUCAUCCAAGUUGUUUUGAGU AUACUCGCUUCAAUACAACUUCCCUU CAUAUUUGAUUCAAGAUUUAAAAUGC AACAACCCCGUGGAAGGAGU | 10 |
| VP40-AUG | Z29337 | 4467-4591 | UCCCAAUCUCAGCUUGUUGAAUUAAU UGUUACUUAAGUCAUUCUUUUUAAAA UUAAUUCACACAAGGUAGUUUGGGUU UAUAUCUAGAACAAAUUUUAAUAUGG CCAGUUCCAGCAAUUACAACA | 11 |
| L-AUG | Z29337 | 11379-11503 | UCAUUCUCUUCGAUACACGUUAUAUC UUUAGCAAAGUAAUGAAAAUAGCCUU GUCAUGUUAGACGCCAGUUAUCCAUC UUAAGUGAAUCCUUUCUUCAAUAUGC AGCAUCCAACUCAAUAUCCUG | 12 |
| NP-AUG | Z29337 | 3-127 | CACACAAAAACAAGAGAUGAUGAUUU UGUGUAUCAUAUAAAUAAAGAAGAAU AUUAACAUUGACAUUGAGACUUGUCA GUCUGUUAAUAUUCUUGAAAAGAUGG AUUUACAUAGCUUGUUAGAGU | 13 |
| Str. Ihn 1(-) | Z29337 | 30-1 | CAAAAUCAUCAUCUCUUGUUUUUGUG UGUC | 14 |

Targeting sequences are designed to hybridize to a region of the target sequence as listed in Table 3. Selected targeting sequences can be made shorter, e.g., 12 bases, or longer, e.g., 40 bases, and include a small number of mismatches, as long as the sequence is sufficiently complementary to allow hybridization with the target, and forms with either the virus positive-strand or minus-strand, a heteroduplex having a $T_m$ of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least the minimum number of bases, e.g., 8-11, preferably 12-15 bases, are complementary to the target sequence. In general, however, facilitated or active uptake in cells is optimized at oligomer lengths less than about 30, preferably less than 25, and more preferably 20 or fewer bases. For PMO oligomers, described further below, an optimum balance of binding stability and uptake generally occurs at lengths of 18-25 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

Table 4 below shows exemplary targeting sequences, in a 5'-to-3' orientation, that target the Ebola Zaire virus (GenBank Acc. No. AF086833) according to the guidelines described above. The sequences listed provide a collection of targeting sequences from which additional targeting sequences may be selected, according to the general class rules discussed above. SEQ ID NOs:16-43 are antisense to the positive strand (mRNA) of the virus whereas SEQ ID NO:15 is antisense to the minus strand viral RNA.

TABLE 4

Exemplary Antisense Oligomer Sequences Targeting Ebola Zaire

| Name | Target GenBank No. AF086833 | Sequence 5'-3' | SEQ ID NO |
|---|---|---|---|
| Str. Inh. 1 | 1-22 (−) strand | CGGACACACAAAAAGAAAGAAG | 15 |
| L-AUG | 11588-11567 | GTAGCCATTTAATATCAAGAGG | 16 |
| L'-AUG | 11581-11600 | TGGGTATGTTGTGTAGCCAT | 17 |
| L-29-AUG | 11552-11573 | CAAGAGGAAGAATTTCAACTGC | 18 |
| L+4-AUG | 11584-11604 | GTATTGGGTATGTTGTGTAGC | 19 |
| L+11-AUG | 11591-11611 | CGTCTGGGTATTGGGTATGTT | 20 |
| VP35-AUG | 3136-3115 | GTTGTCATCTTGTTAGACCAGC | 21 |
| VP35'-AUG | 3133-3152 | CCTGCCCTTTGTTCTAGTTG | 22 |
| VP35-22-AUG | 3032-3053 | GATGAAGGTTTTAATCTTCATC | 23 |
| VP35-19-AUG | 3115-3133 | GTCATCTTGTAGACCAGC | 24 |
| VP35-16-AUG | 3118-3133 | GTCATCTTGTTAGACC | 25 |
| VP35+2-AUG | 3131-3152 | CCTGCCCTTTGTTCTAGTTGTC | 26 |
| NP-AUG | 464-483 | GGACGAGAATCCATACTCGG | 27 |
| NP+4-AUG | 473-495 | CAGATTTTCTGAGGACGAGAATC | 28 |
| NP+11-AUG | 480-499 | CATCCAGATTTTCTGAGGAC | 29 |
| NP+18-AUG | 487-507 | CTCGGCGCCATCCAGATTTTC | 30 |
| NP-19-AUG | 451-472 | CATACTCGGAATTTTGTGATTC | 31 |
| VP40-AUG | 4481-4498 | GGCAATATAACCCGCCTC | 32 |
| VP30-AUG | 8494-8512 | CCATTTAAAAGTTGTCTCC | 33 |
| VP24-AUG | 10331-10349 | GCCATGGTTTTTCTCAGG | 34 |
| VP24-28-AUG | 10317-10336 | CTCAGGTCTTGCTTGGTGTC | 35 |
| VP24+4-AUG | 10348-10369 | TGTATCGTCCCGTAGCTTTAGC | 36 |
| VP24+10-AUG | 10354-10372 | GATTGTATCGTCCCGTAGC | 37 |
| VP24+19-AUG | 10361-10382 | GGCGATATTAGATTGTATCGTC | 38 |
| VP24-5'trm | 10261-10280 | TTCAACCTTGAAACCTTGCG | 39 |
| VP24(8+)-AUG | 10331-10349 | GCCA+TGG+T+T+T+T+TC+TCAGG | 40 |
| VP24-5'trm(6+) | 10261-10280 | +T+TCAACC+T+T+TGAAACC+T+TGCG | 41 |

TABLE 4-continued

Exemplary Antisense Oligomer Sequences Targeting Ebola Zaire

| Name | Target GenBank No. AF086833 | Sequence 5'-3' | SEQ ID NO |
|---|---|---|---|
| panVP35 | 3032-3053 | GATGAAGGTTTTAATCTTCATC | 42 |
| Scrv3 | 4390-4407 8288-8305 | TTTTTCTTAATCTTCATC | 43 |

Figure 2A:
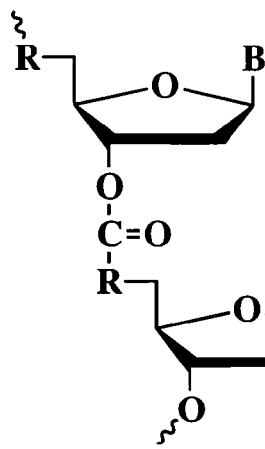
FIGS. 2A-2G show the backbone structures of various oligonucleotide analogs with uncharged backbones and FIG. 2H shows a cationic linkage structure.
Figure 2B:
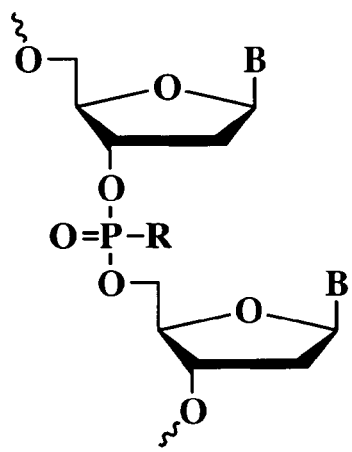
Figure 2C:
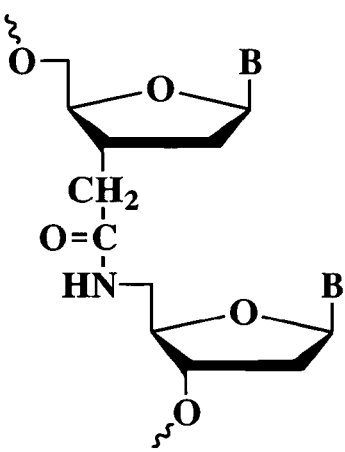
Figure 2D:
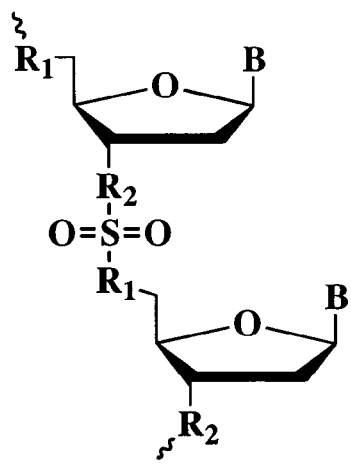
Figure 2E:
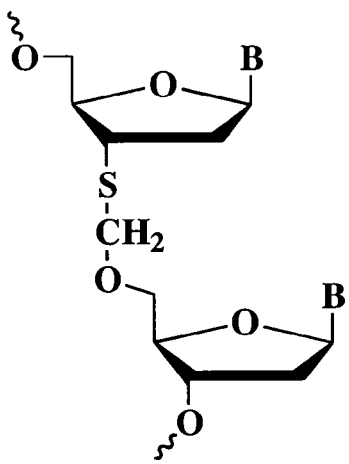
Figure 2F:
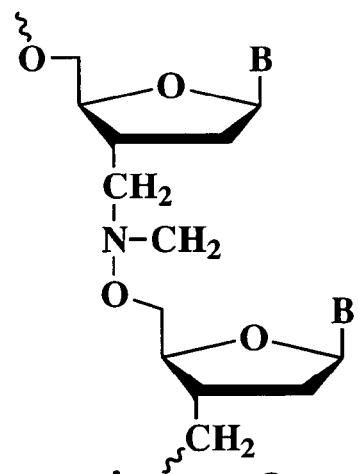
Figure 2G:
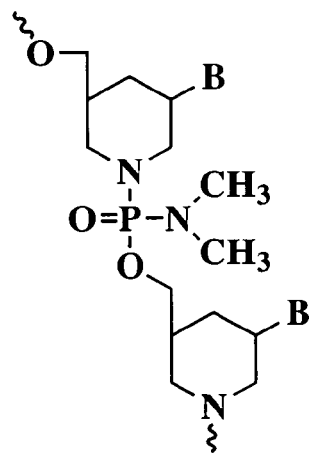
Figure 2H:
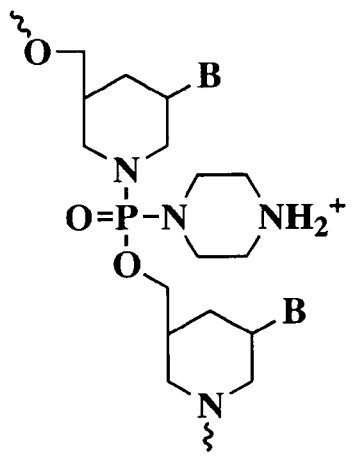

In Table 4, above, SEQ ID NOs:40 and 41 are shown with cationic linkages (+) wherein X=(1-piperazino) as shown in FIG. 1B and FIG. 2H. Also in Table 4, above, SEQ ID NOs: 42 and 43 correspond to antisense oligomers that target the 5' terminal nucleotide region of the Ebola virus VP35 mRNA (SEQ ID NO:42) and the 5' terminal nucleotide region of both the Ebola virus VP40 and VP30 mRNAs (SEQ ID NO:43).

Table 5 below shows exemplary targeting sequences, in a 5'-to-3' orientation, that target the Marburg virus (GenBank Acc. No. Z29337) according to the guidelines described above. The sequences listed provide a collection of targeting sequences from which additional targeting sequences may be selected, according to the general class rules discussed above. SEQ ID NOs:45-58 are antisense to the positive strand (mRNA) of the virus whereas SEQ ID NO:44 is antisense to the minus strand viral RNA.

TABLE 5

Exemplary Antisense Oligomer Sequences Targeting Marburg Virus

| Name | Target GenBank No. Z29337 | Sequence 5'-3' | SEQ ID NO |
|---|---|---|---|
| (−)3'term | 1-21 (−) | GACACACAAAAACAAGAGATG | 44 |
| L-AUG | 11467-11485 | GCTGCATATTGAAGAAAGG | 45 |
| L+7-AUG | 11485-11506 | CATCAGGATATTGAGTTGGATG | 46 |
| VP35-AUG | 2932-2952 | GTCCCACATTGTGAAAATTAT | 47 |
| VP35+7-AUG | 2950-2971 | CTTGTTGCATATATGATGAGTC | 48 |
| NP-AUG | 94-112 | GTAAATCCATCTTTTCAAG | 49 |
| NP-6-AUG | 97-120 | CAAGCTATGTAAATCCATCTTTTC | 50 |
| NP+4-AUG | 106-124 | CCTAACAAGCTATGTAAATC | 51 |
| NP-5'SL | 68-88 | TAACAGACTGACAAGTCTCAA | 52 |
| NP-5'UTR | 44-64 | CAATGTTAATATTCTTCTTTA | 53 |
| NP-5'UTRb | 36-56 | ATATTCTTCTTTATTTATATGT | 54 |
| VP30-AUG | 8852-8873 | GTTGCATTTTAAATCTTGAATC | 55 |
| VP35-5'UTR | 2848-2867 | CCTTTAATATTCTTCGATTT | 56 |
| VP24+5-AUG | 10209-10231 | GTTGTAACGCGTTGATAATTCTG | 57 |
| NP-stem loop | 58-77 | CAAGTCTCAATGTCAATGTT | 58 |

III. Antisense Oligonucleotide Analog Compounds

A. Properties

As detailed above, the antisense oligonucleotide analog compound (the term "antisense" indicates that the compound is targeted against either the virus' positive-sense strand RNA or negative-sense or minus-strand) has a base sequence target region that includes one or more of the following: 1) 125 bases surrounding the AUG start codons of viral mRNA and/or; 2) 30 bases at the 3' terminus of the minus strand viral RNA and/or; 3) 25 bases at the 5' terminus of viral mRNA transcripts. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, or cationic linkages, such as N,N-diethylenediamine phosphoramidates (Dagle, Littig et al. 2000) or 1-piperazino phosphoramidates (FIG. 2H). The net charge is preferably neutral or at most 1-8 net charges per oligomer.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenylanine and cysteine. The use of arginine-rich peptide-PMO conjugates can be used to enhance cellular uptake of the antisense oligomer (See, e.g. (Moulton, Nelson et al. 2004; Nelson, Stein et al. 2005). Exemplary arginine-rich peptides are listed as SEQ ID NOs:61-66 in the Sequence Listing.

In some instances, liposomes may be employed to facilitate uptake of the 30 antisense oligonucleotide into cells. (See, e.g., Williams, S. A., Leukemia 10(12): 1980-1989, 1996; Lappalainen et al., Antiviral Res. 23:119, 1994; Uhlmann et al., "Antisense oligonucleotides: A new therapeutic principle," Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.Y.

and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNAseH

Two general mechanisms have been proposed to account for inhibition of expression by antisense oligonucleotides. (See e.g., (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent applications Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of filovirus viral RNA or mRNA, as described above) the method can be used to detect the presence of a given filovirus, or reduction in the amount of virus during a treatment method.

E. Exemplary Oligomer Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (2A, R═O) and carbamate (2A, R═NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R$_1$, R$_2$═CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F.

Peptide nucleic acids (PNAs) are analogs of DNA in which the backbone is structurally homomorphous with a deoxyribose backbone, consisting of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
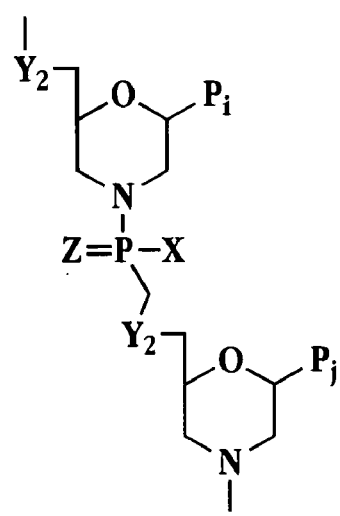
Figure 1D:
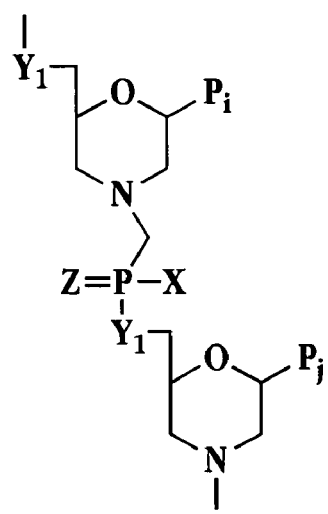

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where $X=NH_2$ or $N(CH_3)_2$, $Y=O$, and $Z=O$.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers. A preferred cationic linkage is 1-piperazino phosphoramidate as shown in FIG. 2H.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Filovirus Replication

Figure 5:
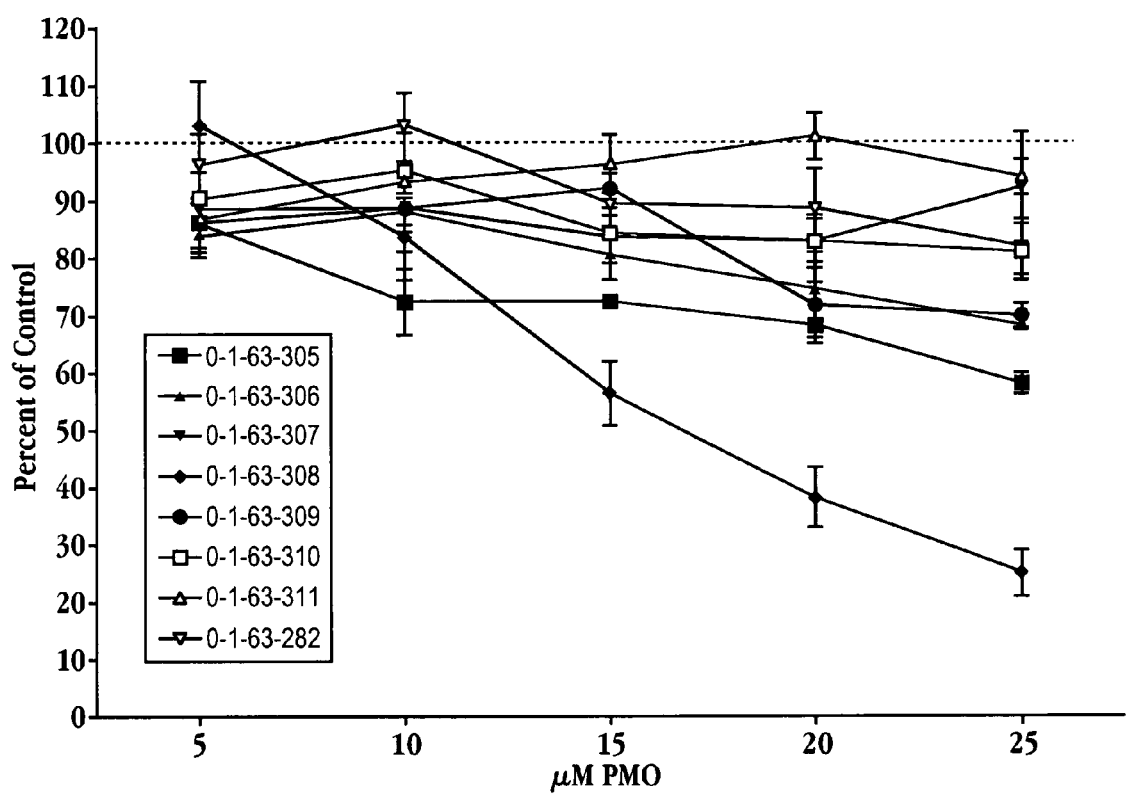
FIG. 5 is a plot showing cytotoxicity in Vero cell culture, expressed as a percent control, as a function of antisense type and concentration.

A. Inhibition in Vero Cells:

PMO antisense compounds and the control PMO (SEQ ID NO:35) were initially evaluated for cytotoxicity when incubated with Vero cells (FIG. 5) in the absence of virus. Only one PMO (0-1-63-308) was found to show dose dependent cytotoxicity in the concentration range of 5 to 25 μM.

Viral titer data were obtained 10 days post-infection of Vero cells. All inhibitors evaluated to date reduce the viral titer, as measured by $TCID_{50}$, to some degree (Table 6 below) but the VP35-AUG inhibitor (SEQ ID NO:21) was the most inhibitory against Ebola virus. The inoculum was taken from cells which received the treatment after infection (15 μM). No serum was added to media during pre-incubation with inhibitor or during infection. After the infection the inoculum was removed and replaced the medium containing 2% serum. The VP35-AUG PMO produced a 3 log reduction in viral titer relative to the no treatment control group. The L-AUG PMO (SEQ ID NO:16) did not produce reduction in viral titer. The L gene is active later in the viral life cycle and the RNA becomes highly bound by NP, VP30 and VP45 proteins so this target may be inaccessible to the L-AUG PMO used in this experiment.

TABLE 6

Viral Titer Reduction in Vero cells

| Treatment (PMO) | $TCID_{50}$ | $TCID_{50}$/ml |
|---|---|---|
| Control (no treatment) | −5.5 | $3.16 \times 10^6$ |
| VP35-scr (SEQ ID NO:60) | −3.2 | $1.47 \times 10^4$ |
| Dscr (SEQ ID NO:59) | −3.8 | $6.81 \times 10^4$ |
| L-AUG (SEQ ID NO:16) | −4.2 | $1.47 \times 10^5$ |
| VP35-AUG (SEQ ID NO:21) | −2.5 | $3.16 \times 10^3$ |

Figure 6A:
FIGS. 6A-6C are photomicrographs of Vero cells in culture (6A) in the absence of Ebola virus infection and antisense treatment; (6B) with Ebola virus infection but no antisense treatment; and (6C) with Ebola virus infection and treatment with VP35-AUG (SEQ ID NO:17) antisense compound.
Figure 6B:
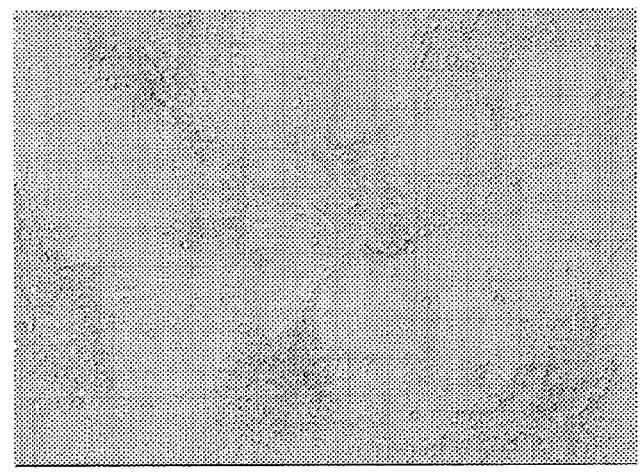
Figure 6C:
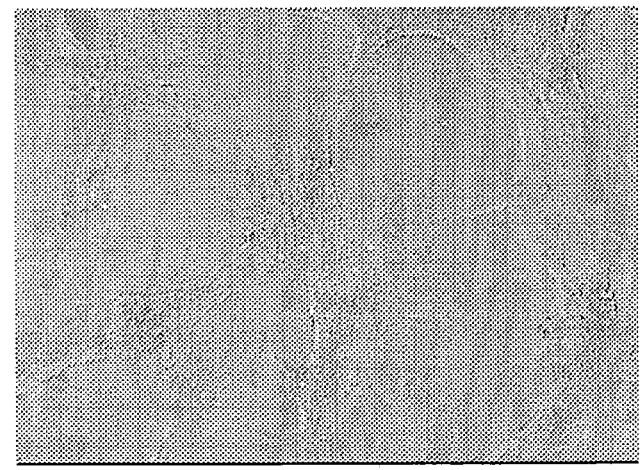

Vero cells were pretreated with different concentrations of the PMO (namely 0.1, 0.5, 1.0, 2.5, 5.0 and 10 μM), infected with EBOV for 1 h and the same concentration of PMO was added back afterwards. The 1 μM concentration of VP35-AUG (SEQ ID NO:21) inhibitor reduced the cytopathic effect (CPE) significantly compared to 0.5 μM concentration. The reduction in CPE has been repeatedly observed in culture and an example of these studies is seen in FIGS. 6A-6C for non-infected (FIG. 6A), infected, no treatment (FIG. 6B), and infected and treated (FIG. 6C).

B. Treatment in Infected Mice

These observations involved C57BL mice treated intraperitoneally (IP) with PMO at −24 and −4 hours prior to viral challenge at time 0. Each treatment group is composed of 10 male mice. The Ebola Zaire infection involves 100 pfu injected IP and death is the endpoint observed between days 7 and 10 post infection. A summary of studies to date is provided in Table 7. The dose×2 indicates the dose given at the two times prior to viral infection. The VP35-AUGcon compound refers to the VP35-AUG PMO that has been conjugated with the arginine-rich peptide $R_9F_2C$ (SEQ ID NO:61).

TABLE 7

Summary of Treatment in Mice

| Group | Dose | Survivors/challenged |
|---|---|---|
| Saline | na | 1/10 |
| Str. Ihn 1 (SEQ ID NO:15) | 0.5 mg × 2 | 0/10 |
| VP35-AUG (SEQ ID NO:21) | 0.5 mg × 2 | 6/10 |
| Saline | na | 0/10 |
| Str. Ihn 1 (SEQ ID NO:15) | 1.0 mg × 2 | 2/10 |
| VP35-AUG (SEQ ID NO:21) | 1.0 mg × 2 | 7/10 |
| Scramble (SEQ ID NO:60) | 1.0 mg × 2 | 1/10 |
| VP35-AUG + Str Inh 1 | 1.0 mg × 2 | 6/10 |

TABLE 7-continued

Summary of Treatment in Mice

| Group | Dose | Survivors/challenged |
|---|---|---|
| (SEQ ID NOs:21 and 15) VP35-AUG-P003 + VP35-AUG (SEQ ID NO:21 + 61 and 21) | 0.5 mg + 1.0 mg | 9/10 |
| VP35-AUG-P003 (SEQ ID NO:21 + 61) | 0.5 mg × 2 | 9/10 |

Mice that survived the viral challenge described in TABLE 7 were rechallenged with virus to determine the immunological consequence of treatment. The results of the first studies are summarized in TABLE 8.

TABLE 8

Rechallenge Studies in Mice

| Group | Earlier dose | Survivors/challenged |
|---|---|---|
| Saline | na | 0/10 |
| Str. Ihn 1, 0-1-63-412 | 0.5 mg × 2 | 1/2 |
| VP35, 0-1-63-413 | 0.5 mg × 2 | 6/6 |
| VP35, 0-1-63-413 | 1.0 mg × 2 | 7/7 |

All survivors from earlier Ebola challenge studies were evaluated in re-challenge studies 2 to 4 weeks after the initial viral exposure. The MOI for the re-challenge was identical to the initial challenge. All of the re-challenged survivors from therapeutic treatment with the PMO targeting VP35-AUG survived the re-challenge. These observations suggest viral replication was initiated in the viral challenge leading to a robust immune response, essentially a perfect vaccination. In accordance with another aspect, the invention includes a method of vaccinating a mammalian subject against Ebola virus by (i) pretreating the subject with antisense to Ebola virus, e.g., administering a VP35 antisense or compound combination at one or two times prior to Ebola virus challenge, and (ii) challenging the individual with the virus, preferably in an attenuated form incapable of producing serious infection.

Figures 7, 8:
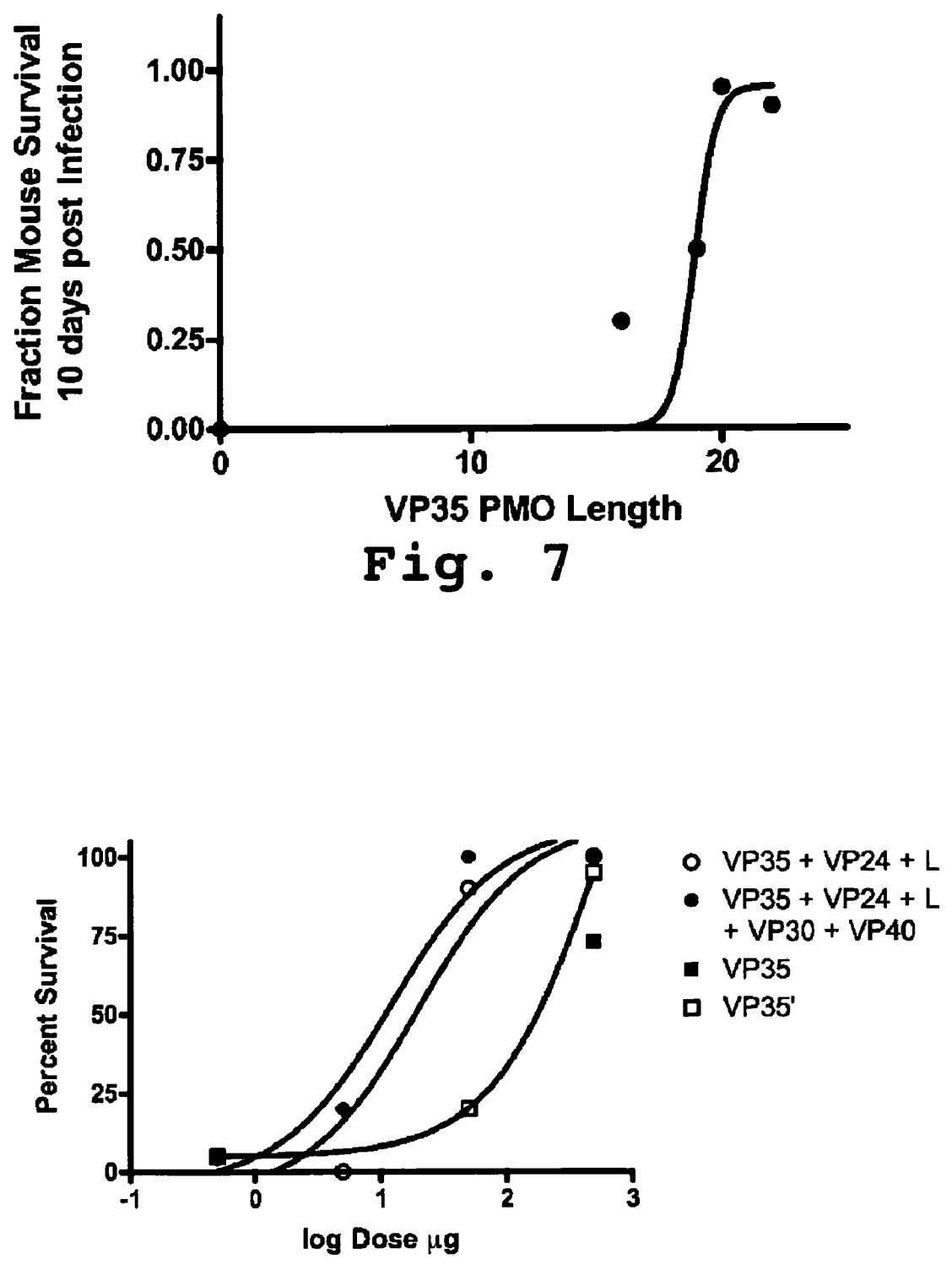

Similar treatment methods were aimed at determining the optimal length for anti-Ebola PMO antisense, employing various length VP35 antisense PMO. As seen from the data below (Table 9) and the plot in FIG. 7, the 16-mer is less effective than the 19-mer which is less effective than the 22-mer which is in the same order as the predicted Tm.

TABLE 9

Studies to Identify Optmal VP35-AUG Targeting Sequence

| Group | AVI Number | Survivors/challenged* |
|---|---|---|
| Saline | NA | 1/10 |
| VP35scr | SEQ ID NO:60 | 1/10 |
| VP35-16 | SEQ ID NO:25 | 3/10 |
| VP35-19 | SEQ ID NO:24 | 5/10 |
| VP35-22 | SEQ ID NO:23 | 9/10 |
| VP35'-AUG | SEQ ID NO:22 | 10/10; 9/10 |

*Observations as of day 9 post challenge

Antisense compounds against six of the seven different genes expressed by Ebola were evaluated in the mouse model in a head-to-head experiment. (The GP gene was not included). As seen in Table 10, below, the most effective PMOs target VP24 and VP35 with L, VP40 and VP30 demonstrating less robust but significant activity in reducing mortality. The mice treated with VP40 died later than controls and those that survived appeared to be less active. These data indicate differences in the efficacy for the different gene targets. As single antisense compounds, the antisense against VP35 and VP24 are preferred therapeutic agents.

TABLE 10

Comparison of Ebola Gene Targets

| Target | SEQ ID NO | Survivors/challenged* |
|---|---|---|
| NP-AUG | 27 | 2/10 |
| VP40-AUG | 32 | 5/10 |
| VP30-AUG | 33 | 5/10 |
| VP24-AUG | 34 | 10/10; 5/10 |
| L'-AUG | 17 | 6/10; 2/10 |
| VP35-22 | 23 | 9/10 |
| Scramble | 60 | 0/10; 0/10 |
| PBS | NA | 1/10; 0/10 |

*Dose 0.5 mg IP at −24 and −4 hours to challenge, second survival numbers are from repeat experiment with fresh virus preparation.

In one embodiment, the antisense compound is administered in a composition (or separately) in combination with one or more other antisense compounds. One preferred combination is VP35-AUG (SEQ ID NO:21) plus VP24-AUG (SEQ ID NO:34); another is VP35-AUG, VP24-AUG and L-AUG (SEQ ID NOs:21, 34 and 16, respectively). As seen in Table 11 below, and as plotted in FIG. 8, the dose response curves for a combination of the 3 compounds (VP35-AUG, VP24-AUG and L-AUG, each given IP at 0.5 mg/dose) is not different from 5 different compounds (VP35-AUG, VP24-AUG, L-AUG, VP24-AUG and VP40-AUG). The dose of 0.5 mg/mouse provides 100 percent survival from either combination. Further, these data indicate the $EC_{50}$ for combination therapy is between 10 and 30 μg/mouse and that the $EC_{90}$ is approximately 50 μg/mouse.

TABLE 11

Combination Treatment for *Ebola*

| Group | SEQ ID NOs | Survivors/Challenged |
|---|---|---|
| PBS | NA | 0/10 |
| NP-AUG, VP40-AUG, VP30-AUG, VP24-AUG, and L'-AUG | 27, 32-34 and 17 | 9/10 |
| NP-AUG, VP40-AUG, VP30-AUG, VP24-AUG, L'-AUG and VP35-AUG | 27, 32-34, 17 and 21 | 10/10 |
| VP35-AUG, VP24-AUG and L'-AUG | 21, 34 and 17 | 10/10 |
| VP35-AUG, VP24-AUG, L'-AUG, VP40-AUG and VP30-AUG | 21, 34, 17, 32 and 33 | 10/10 |

*Each agent in the combination administered 0.5 mg via IP route.

The success with 100 percent survival from a single IP injection 24 hours after Ebola infection (via IP route) indicates the antisense mechanism can suppress virus after viral replication has distributed throughout the body and that these agents can be used as therapy for infected individuals (Table 12 and FIG. 9). The comparison of dose-response in the −24 and −4 hour regimen between VP35-AUG only and the 3 agent combination is clear evidence of synergy. The combination could be more effective at 0.1×the dose than a single agent.

TABLE 12

Comparison of Dose Regimens

| Treatment | Dose (mg) | −24 and −4 hours | −4 hours only | +24 hours |
|---|---|---|---|---|
| VP35-AUG | 0.5 | 9/10 | | |
| (SEQ ID NO:21) | 0.05 | 4/10 | | |
| VP35-AUG, VP24-AUG | 0.5 | 10/10 | 10/10 | 10/10 |
| and L'-AUG | 0.05 | 10/10 | 4/10 | 5/10 |
| (SEQ ID NOs:21, 34 | 0.005 | | 0/10 | 4/10 |
| &17) | | | | |

V. Treatment Method

The antisense compounds detailed above are useful in inhibiting Ebola viral infection in a mammalian subject, including human subjects. Accordingly, the method of the invention comprises, in one embodiment, contacting a cell infected with the virus with an antisense agent effective to inhibit the replication of the virus. In one embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific Ebola strain causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Another method for identifying the Ebola viral strain employs one or more antisense oligomers targeting specific viral strains. In this method, (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The viral strain is identified based on the presence (or absence) of a heteroduplex comprising the antisense oligomer and a complementary portion of the viral genome of the given known virus or family of viruses. Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., Leukemia 10(12): 1980-1989, 1996; Lappalainen et al., Antiviral Res. 23:119, 1994; Uhlmann et al., "Antisense oligonucleotides: A new therapeutic principle," Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 5-1000 mg oligomer or oligomer cocktail per 70 kg individual. In some cases, doses of greater than 500 mg oligomer/patient may be necessary. For i.v., i.p or s.q. administration, preferred doses are from about 100-1000 mg oligomer or oligomer cocktail per 70 kg body weight. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

EXAMPLES

Materials and Methods:

Synthesis of PMOs. PMOs were designed with sequence homology near or overlapping the AUG start site of Ebola virus VP35 (VP35'-AUG, SEQ ID NO:22), VP24 (VP24-AUG, SEQ ID NO:36), and L (L'-AUG, SEQ ID NO:17). Unrelated, scrambled PMOs (SEQ ID NOs:59 and 60) were used as a control in all experiments. The PMOs were synthesized by AVI Biopharma, Inc. (Corvallis, Oreg.), as previously described (Summerton and Weller 1997).

In vitro translation assay. The protein coding sequence for firefly luciferase, without the initiator-Met codon ATG, was subcloned into the multiple cloning site of plasmid pCiNeo (Promega). Subsequently, complementary oligonucleotides for Ebola virus VP35 (−98 to +39 bases 3020 to 3157), Ebola virus VP24 (−84 to +43 or bases 10261 to 10390), Ebola virus L (−80 to +49 or bases 11501 to 11632) were duplexed and subcloned into Nhe 1 and Sal 1 sites. RNA was generated from the T7 promoter with T7 Mega script (Ambion, Inc., Austin, Tex.). The in vitro translations were carried out by mixing different concentrations of PMO with 6 nM RNA. A sigmoidal curve to determine the $EC_{50}$ values was generated with the observed luciferase light emission (n=3 per PMO concentration) and the PMO concentration.

Ebola virus infection of PMO-treated animals. C57B1/6 mice, aged 8-10 weeks of both sexes, were obtained from National Cancer Institute, Frederick Cancer Research and Development Center (Frederick, Md.). Mice were housed in microisolator cages and provided autoclaved water and chow ad libitum. Mice were challenged by intraperitoneal injection with ~1000 pfu of mouse-adapted Ebola virus diluted in phosphate buffered saline (PBS) (Bray, Davis et al. 1998). Mice were treated with a combination of 1 mg, 0.1, or 0.01 mg of each of the VP24-AUG, L'-AUG and VP35'-AUG PMOs (SEQ ID NOs:34, 17 and 22, respectively) or the scramble control PMO (SEQ ID NO:60) either split between two equivalent doses at 24 and 4 hours prior to Ebola virus challenge or a single dose 24 hours after challenge. C57B1/6 mice were challenged intraperitoneally with 1000 plaque-forming units of mouse-adapted Ebola virus (Bray, Davis et al. 1998). Hartley guinea pigs were treated intraperitoneally with 10 mg of each of the VP24-AUG, VP35'-AUG, and L'-AUG PMOs 24 hours before or 24 or 96 hours after subcutaneous challenge with 1000 pfu of guinea-pig adapted Ebola virus (Connolly, Steele et al. 1999). Female rhesus macaques of 3-4 kg in weight were challenged with ~1000 pfu of Ebola virus ('95 strain) (Jahrling, Geisbert et al. 1999) by intramuscular injection following PMO treatment. The monkeys were treated from days −2 through day 9 via a combination of parenteral routes as shown in FIG. 10. The dose of the VP24-AUG PMO was 12.5-25 mg at each injection and the dose of the VP35'-AUG and L'-AUG PMOs ranged from 12.5-100 mg per injection.

Example 1

Antiviral Efficacy of Ebola Virus-specific PMOs in Rodents

Figure 11A:
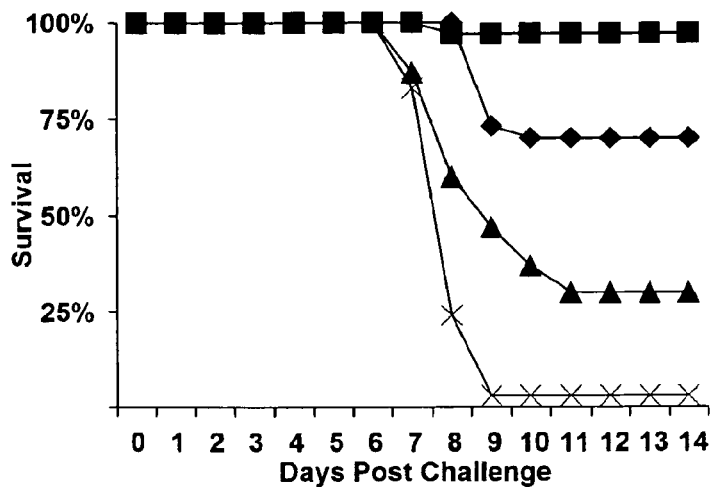
FIG. 11 shows Ebola-specific PMOs protect mice from lethal Ebola virus infection. (A) Survival of mice pretreated at 4 and 24 hours before EBOV infection with 500 μg of PMOs targeting VP24 (♦), VP35 (■), L (▲), or with an unrelated sequence (X). (B) Survival of mice pretreated with 1 mg (◊), 0.1 mg (□), or 0.01 mg (Δ) of a combination of the VP24, VP35, and L) PMOs or 1 mg (♦), 0.1 mg (■), or 0.01 mg (▲) of VP35 PMO only or an unrelated sequence (X). (C) Survival in mice treated 24 hours following EBOV infection with 1 mg (♦), 0.1 mg (■), or 0.01 mg (▲) of the combination of PMOs or an unrelated sequence (X). (D-G) C57Bl/6 mice were challenged intraperitoneally with 1000 plaque-forming units of EBOV following treatment with PMOs. Immunoperoxidase stain is brown with hematoxylin counterstain. Viral antigen within the spleen (100×) of a mouse treated with scrambled PMO (D) or the EBOV PMOs (E) three days after EBOV infection. Diffuse staining pattern in the livers (600×) of the scrambled PMO-treated mice (F) on day 6 of EBOV infection, compared to focal areas of infection in the mice treated with the combination of PMOs (G).
Figure 11B:
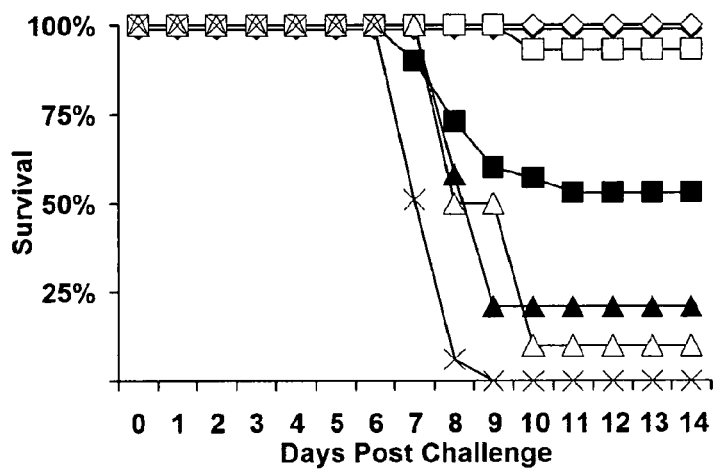
Figure 11C:
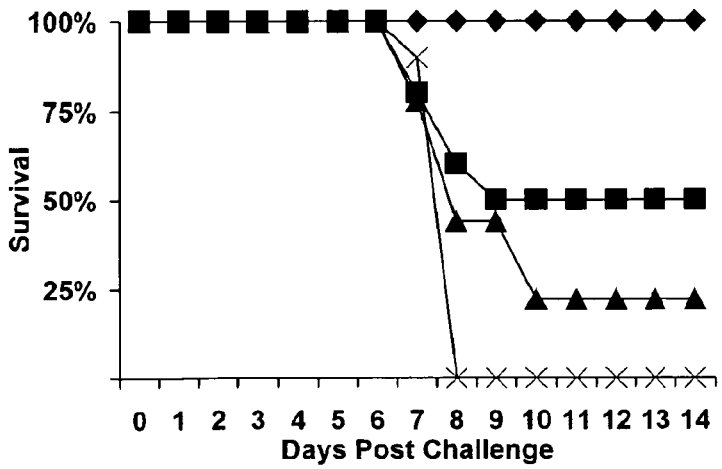
Figure 11D:
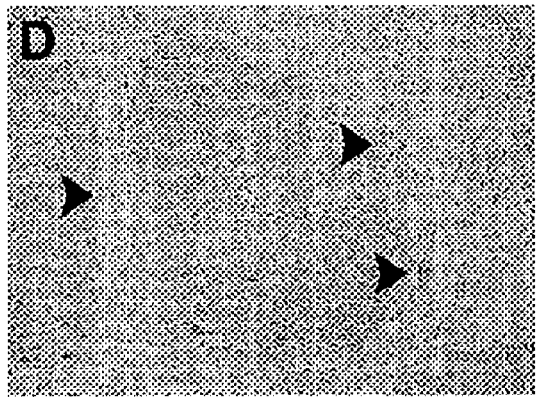
Figure 11E:
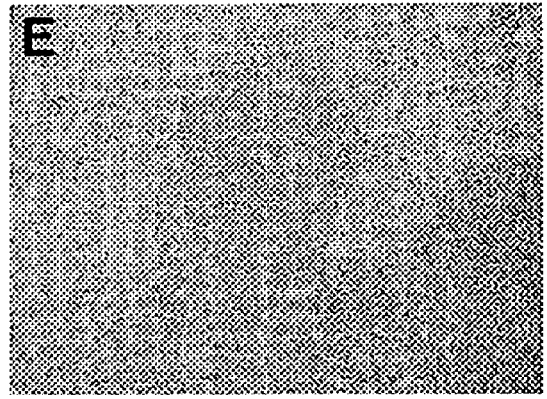
Figure 11F:
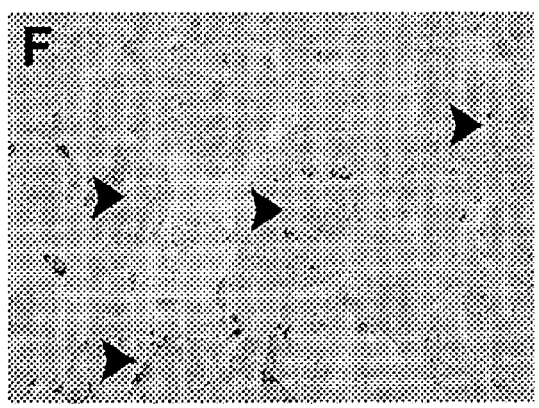
Figure 11G:
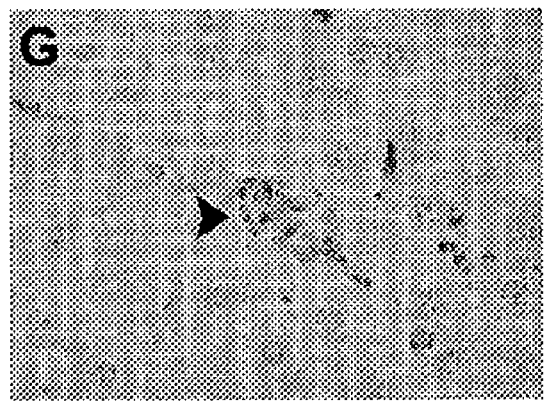
Figure 12:
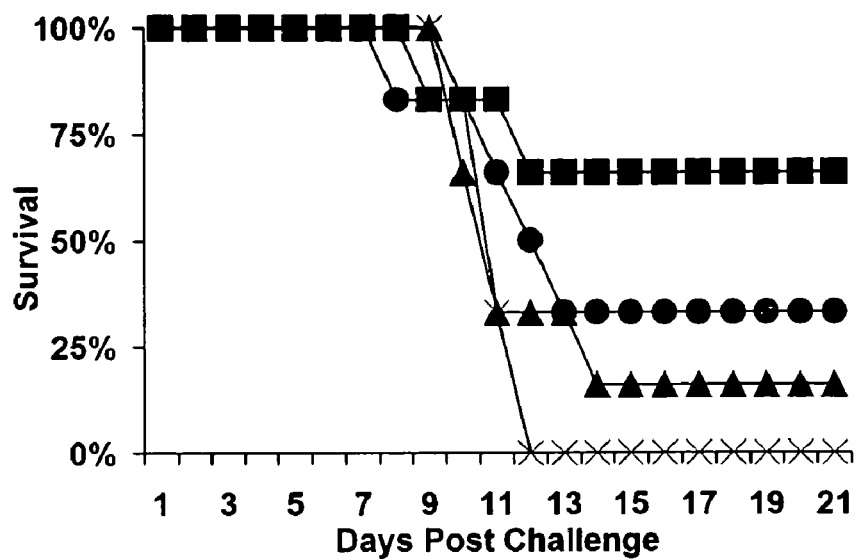
FIG. 12 shows that treatment of guinea pigs with antisense PMOs increases survival following lethal Ebola virus infection. Hartley guinea pigs were treated intraperitoneally with 10 mg each of VP24, VP35, and L PMO in PBS at −24 (▲), +24 (●), or +96 (■) hours post challenge. Control guinea pigs were injected with PBS only (X). The guinea pigs were infected subcutaneously with ~1000 pfu of EBOV and monitored for illness for 21 days. The data are presented as percent survival for each group (n=6).

To determine the in vivo efficacy of the Ebola virus-specific PMOs, the survival of mice treated with 500 µg doses of the individual PMOs (VP24-AUG, L'-AUG and VP35'-AUG, SEQ ID NOs:34, 17 and 22, respectively) at 24 and 4 hours before challenge with 1000 plaque-forming units (pfu) of mouse-adapted Ebola virus was determined. The VP35'-AUG, VP24-AUG and L'-AUG PMOs exhibited a wide range of efficacy against lethal EBOV infection and the VP35'-specific PMO provided nearly complete protection (FIG. 11A). Next, we performed a dose response experiment with the VP35 PMO and found that reducing the dose of the PMO from 1,000 to 100 µg reduced the efficacy substantially (FIG. 11B). Hence, to further enhance efficacy, we decided to use a combination of all three PMOs. This combination of PMOs administered 24 and 4 h before lethal Ebola virus challenge resulted in robust protection and showed substantial enhancement in protection afforded by the VP35 PMO alone, especially at lower doses (FIG. 11B). To determine the efficacy of the combination of PMOs in a post-challenge treatment regimen, mice were injected with 1,000 pfu of Ebola virus and were treated the next day with the PMOs (FIG. 11C). Mice that were given a single dose of 1,000 µg 24 h after the lethal challenge and survival was scored for 14 days. Again, Ebola virus-infected mice were fully protected and lower doses showed substantial protection as compared to the control PMO. To determine the effectiveness of the PMO treatment in Ebola virus-infected guinea pigs, the combination of PMOs was administered 24 hours before or 24 or 96 hours after EBOV infection. Survival was greatly increased in guinea pigs receiving the PMOs either 24 or 96 hours after infection, as compared to untreated or pretreated guinea pigs as shown in FIG. 12.

Figure 13:
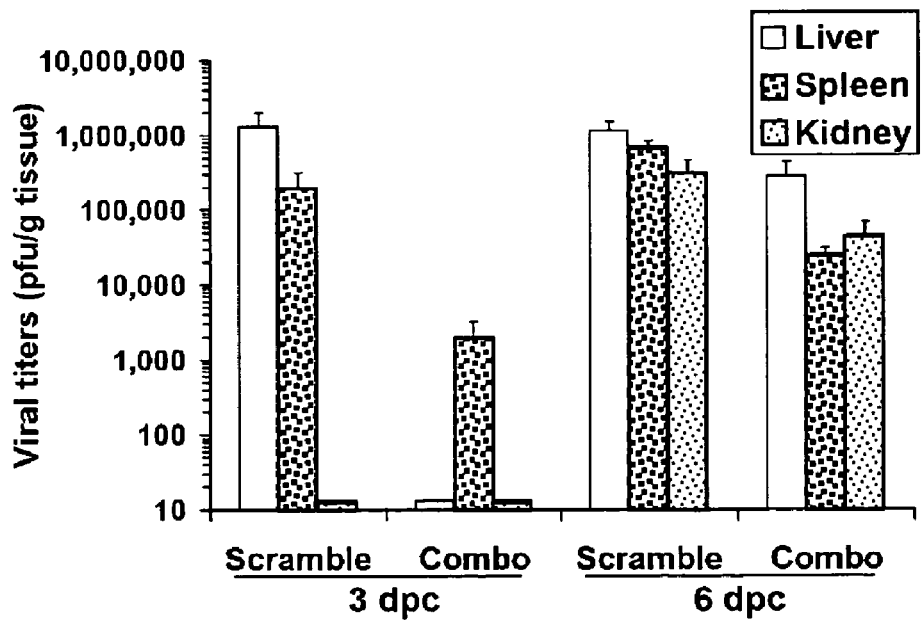
FIG. 13 shows that Ebola-specific PMOs reduce viral replication in vivo. Viral titers in tissues from mice treated with a combination of PMO and infected with 1000 pfu of EBOV. Samples of the liver, spleen, and kidney were taken at 3 or 6 days post challenge (dpc), macerated, and analyzed for viral titer using plaque assay. The data are presented as the mean viral titer of 3 mice with error bars representing the standard deviation.
Figures 14B, 14C:
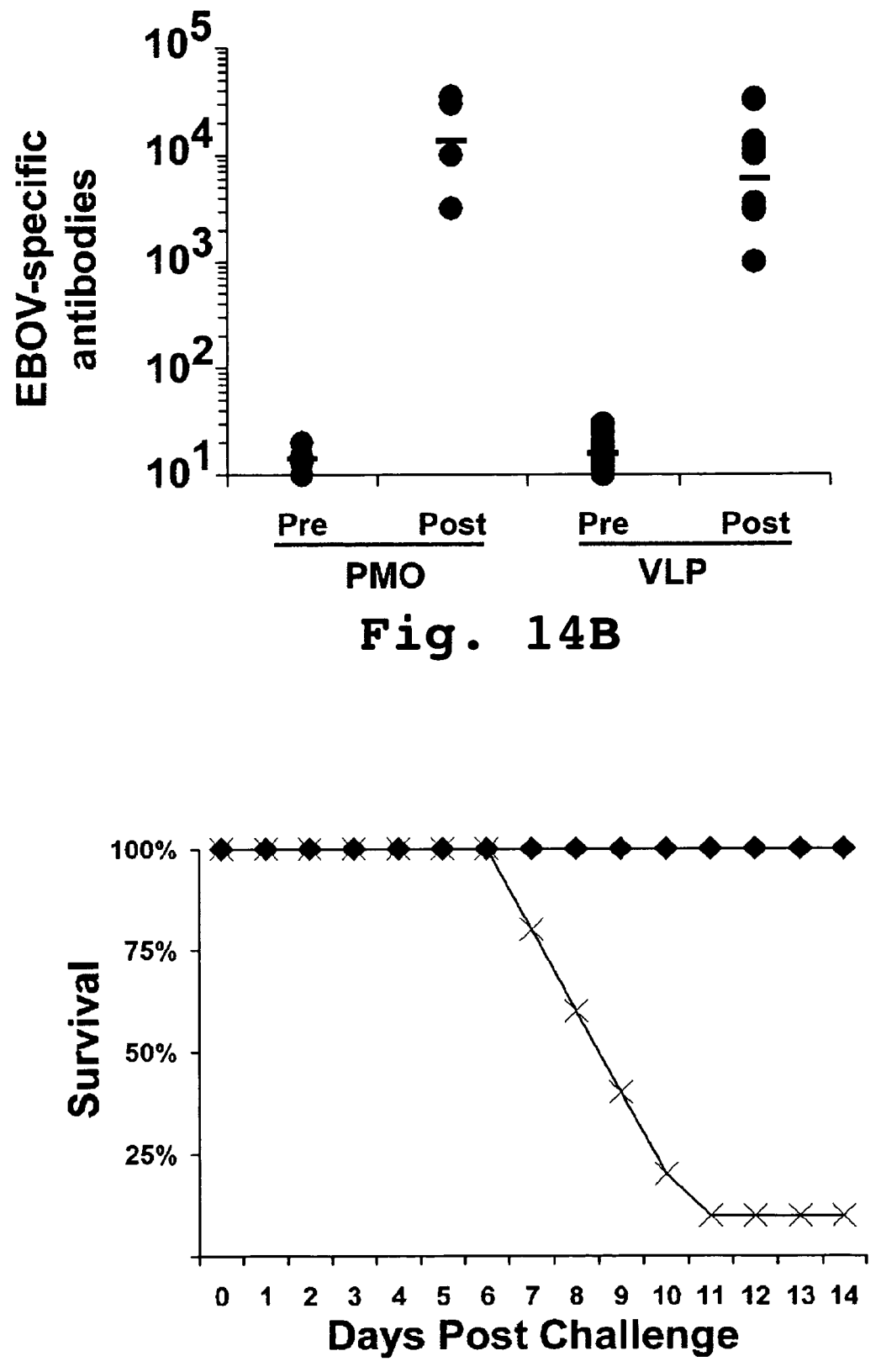

Examination of tissues shortly following infection showed that treatment of mice with the combination of Ebola virus-specific PMO slowed viral spread compared to mice treated with the scrambled PMO. Three days after the infection, multiple foci of infected cells were easily observed in the spleens of the mice treated with the scrambled PMO (FIG. 13D). In contrast, very few EBOV-infected cells could be found in the spleens of the anti-EBOV PMO-treated mice (FIG. 13E). Six days after viral inoculation, the infection was fulminant in the spleens of all animals (data not shown) and had spread to the livers of both mice treated with scrambled and combination PMOs (FIGS. 13F and 13G). However, the extent of the infection was limited in the combination PMO-treated mice, and, unlike the scrambled PMO-treated mice, EBOV antigen was not detectable within their hepatocytes, (FIGS. 13F and 13G). The observed pattern of antigen staining within the tissues was corroborated by the viral titers as shown in FIG. 14.

Figure 15A:
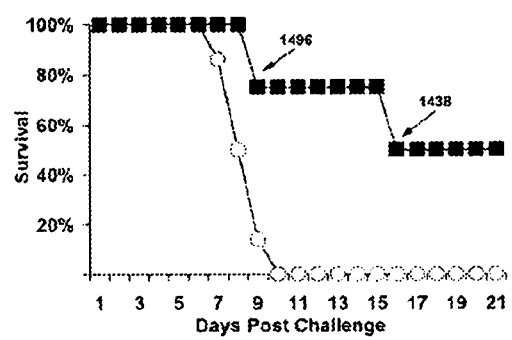
FIG. 15 shows that treatment of rhesus macaques with antisense PMOs provide protection against lethal Ebola virus infection. (A) Survival following infection with 1000 pfu of EBOV in monkeys treated with a combination of PMOs (■) or untreated monkeys (○). The arrows indicate the monkeys that died at the time indicated. (B-D) Viral titers (B), platelet counts (C), or alkaline phosphatase levels (D) in the blood of the PMO-treated monkeys [0646 (◆), 1438 (▲), 1496 (X), 1510 (■)] or an untreated monkey (○).
Figure 15B:
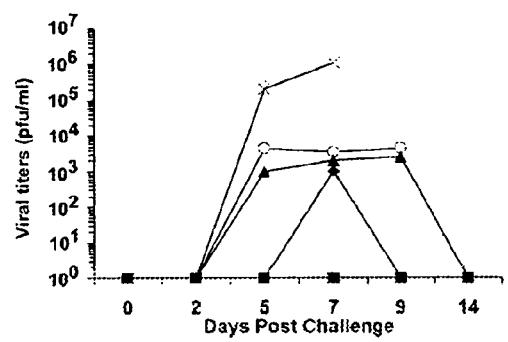
Figure 15C:
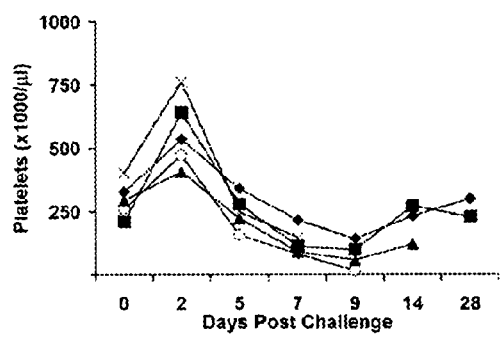
Figure 15D:
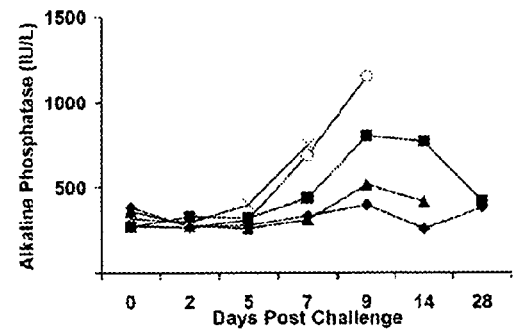

To determine whether mice treated with the PMO therapeutics generated immune responses to Ebola virus, they were tested for Ebola virus-specific cell-mediated and humoral immune responses. Four weeks after infection, the mice demonstrated both CD4+ and CD8+ T cell responses to multiple Ebola virus peptides, including NP and VP35 as shown in FIG. 15A. They also generated strong serum Ebola virus-specific antibody responses that were similar to the post-challenge antibody responses of mice protected by a therapeutic Ebola virus-like particle vaccine as shown in FIG. 15B (Warfield, Perkins et al. 2004). To study if the generated immune responses were protective, PMO-treated mice were rechallenged with another dose of 1,000 pfu of Ebola virus four weeks after surviving the initial challenge and these mice were completely protected from a second lethal Ebola virus infection as shown in FIG. 15C.

Example 2

Antiviral Efficacy of Ebola Virus-specific PMOs in Non-human Primates

Based on the encouraging results both in vitro and in rodents, a trial in nonhuman primates was performed. Four rhesus monkeys were treated with PMO from two days prior to Ebola virus infection through day 9 of the infection. The naive control monkey in this experiment received no treatment and succumbed to Ebola virus infection on day 10 as shown in FIG. 16A. Of 12 rhesus monkeys that have been infected in the inventors' laboratory with the same seed stock of virus, all died of Ebola virus between days 7 and 10 as shown in FIG. 16A. One of the PMO-treated monkeys succumbed to the infection on day 10. A second PMO-treated monkey cleared the EBOV infection from its circulation between days 9 and 14, but was unable to recover from disease and died on day 16 as shown in FIGS. 16A and 16B. The two surviving monkeys had no symptoms of disease beyond mild depression until day 35, at which time they were euthanized. Incorporating historical controls, there were significant differences in survival curves between groups (p=0.0032). The mean survival time for the treatment group was 14.3 days with a standard error of 2.1 days. The mean survival time for the control group was 8.3 days with a standard error of 0.2 days. The overall survival rate demonstrated a significant p value of 0.0392, when compared to historical data.

There were early clinical signs or laboratory values that correlated with survival. The laboratory tests that most closely predicted survival were viral titers, platelet counts, and liver-associated enzymes in the blood. The monkeys that did not survive infection had detectable virus by day 5, in stark contrast to the PMO-treated monkeys that survived, which had little to no viremia on day 5 (FIG. 16B). As expected in a hemorrhagic disease, both the PMO-treated and naive monkeys exhibited thrombocytopenia. However, the PMO-treated monkeys that survived did not have platelet counts far below 100,000 at any time, and their platelet counts began to recover coincident with viral clearance (FIG. 16C). Similarly, all the monkeys experienced increases in their liver-associated enzyme levels, including alkaline phosphatase. However, the levels in the surviving monkeys did not climb as high as those that succumbed to the infection, and they returned to normal levels within the month after the EBOV infection (FIG. 16D). No correlation was found between survival and multiple other hematological values, body temperature, serum cytokines, or fibrin degradation products. Since the surviving PMO-treated monkeys had low to undetectable viremias following infection, we assessed the immune responses of the surviving monkeys. By 28 days after Ebola virus challenge, the surviving rhesus monkeys had high levels of both anti-EBOV antibodies and T cell responses, similar to the PMO-protected mice.

Example 3

Increased Antisense of Activity Using PMO with Cationic Linkages

Figure 16:
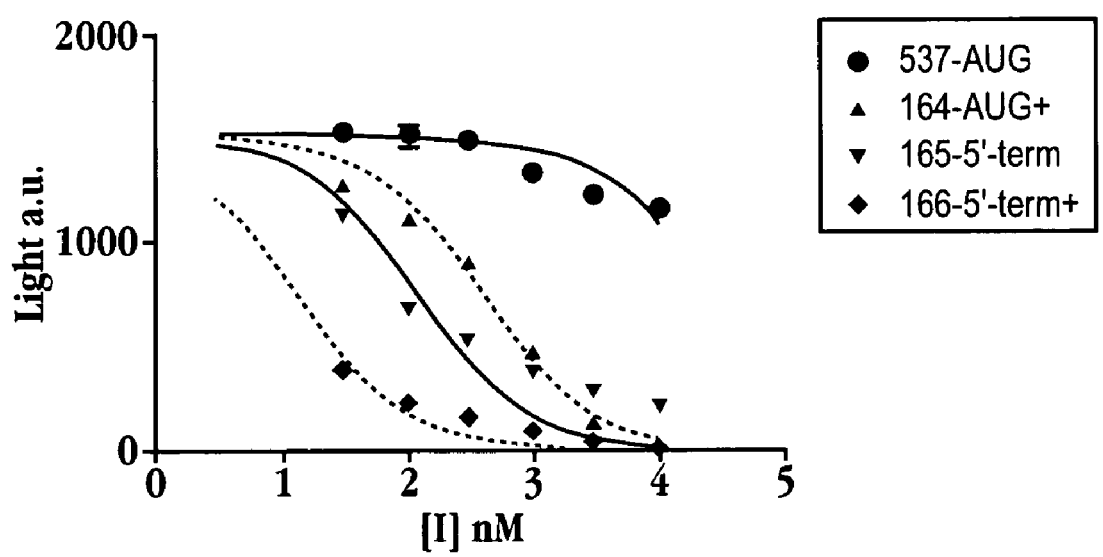
FIG. 16 shows the increased antisense activity of PMOs with cationic linkages targeting the EBOV VP24 mRNA in a cell free translation assay. PMOs used were 537-AUG (SEQ ID NO:34), 164-AUG+ (SEQ ID NO:40), 165-5'-term (SEQ ID NO:39) and 166-5'-term+ (SEQ ID NO:41).

Two PMOs were synthesized using cationic linkages for a subset of the oligomer linkages as shown in Sequence Listing for SEQ ID NOs:40 and 41. These oligomers incorporated the cationic linkage (1-piperazino phosphoramidate) shown in FIG. 2H at the positions indicated with a "+". These two PMOs target the EBOV VP24 mRNA. A cell free translation assay was performed using the VP24:luciferase mRNA as the input RNA. PMO with and without cationic linkages were compared for their ability to inhibit luciferase expression and the results are shown in FIG. 16. Compared to the uncharged PMO with the same base sequence, the PMOs with between 6 and 8 cationic linkages demonstrated between 10 and 100-fold increased antisense activity in this assay.

Based on the experiments performed in support of the invention as described above in the Examples, efficacious anti-filovirus PMOs have been identified. The antiviral PMOs demonstrate favorable anti-Ebola viral activity both in vitro and in vivo in both rodents and non-human primates. Together, the compounds and methods of the present invention provide a highly efficacious therapeutic treatment regimen for lethal Ebola virus infections. PMOs have already been tested in clinical trials and have appropriate pharmacokinetic and safety profiles for use in humans (Arora and Iversen 2001). The results presented here have far-reaching implications for the treatment of highly lethal Ebola virus hemorrhagic fever, as well as diseases caused by other filovirus biothreats including Marburg virus.

Sequence Listing Table

| AVI No. | Name | Target Sequences (5'-3') | SEQ ID NO |
|---|---|---|---|
| NA | VP35-AUG | AAUGAUGAAGAUUAAAACCUUCAUCAUC CUUACGUCAAUUGAAUUCUCUAGCACUC GAAGCUUAUUGUCUUCAAUGUAAAAGAA AAGCUGGUCUAACAAGAUGACAACUAGA ACAAAGGGCAGGG | 1 |
| NA | VP24-AUG | CGUUCCAACAAUCGAGCGCAAGGUUUCAA GGUUGAACUGAGAGUGUCUAGACAACAAA AUAUUGAUACUCCAGACACCAAGCAAGAC CUGAGAAAAAACCAUGGCUAAAGCUACGG GACGAUACA | 2 |
| NA | VP30-AUG | AGAUCUGCGAACCGGUAGAGUUUAGUUGC AACCUAACACACAUAAAGCAUUGGUCAAA AAGUCAAUAGAAAUUUAAACAGUGAGUGG AGACAACUUUUAAAUGGAAGCUUCAUAUG AGAGGAC | 3 |
| NA | VP40-AUG | AAACCAAAAGUGAUGAAGAUUAAGAAAAA CCUACCUCGGCUGAGAGAGUGUUUUUUCA UUAACCUUCAUCUUGUAAACGUUGAGCAA AAUUGUUAAAAAUAUGAGGCGGGUUAUAU UGCCUACUG | 4 |
| NA | L-AUG | GUAGAUUAAGAAAAAAGCCUGAGGAAGAU UAAGAAAAACUGCUUAUUGGGUCUUUCCG UGUUUUAGAUGAAGCAGUUGAAAUUCUUC CUCUUGAUAUUAAAUGGCUACACAACAUA CCCAAUAC | 5 |
| NA | NP-AUG | UGAACACUUAGGGGAUUGAAGAUUCAACA ACCCUAAAGCUUGGGGUAAAACAUUGGAA AUAGUUAAAAGACAAAUUGCUCGGAAUCA CAAAAUUCCGAGUAUGGAUUCUCGUCCUC AGAAAAUCU | 6 |
| NA | Str. Ihn 1(-) | UAAAAAUUCUUCUUUCUUUUGUGUGUC CG | 7 |
| NA | VP35-AUG | CUAAAAAUCGAAGAAUAUUAAAGGUUUUC UUUUAUAUUCAGAAAAGGUUUUUUAUUCU CUUCUUUCUUUUUGCAAACAUAUUGAAAU AAUAAUUUUCACAUGUGGGACUCAUCAU AUAUGCAAC | 8 |
| NA | VP24-AUG | UUCAUUCAAACACCCCAAAUUUUCAAUCA UACACAUAAUAACCAUUUUAGUAGCGUUA CCUUUCAAUACAAUCUAGGUGAUUGUGAA AAGACUUCCAAACAUGGCAGAAUUAUCAA CGCGUUACA | 9 |
| NA | VP30-AUG | GAAGAACAUUAAGUGUUCUUUGUUAGAAU UAUUCAUCCAAGUUGUUUUGAGUAUACUC GCUUCAAUACAACUUCCCUUCAUAUUUGA UUCAAGAUUUAAAAUGCAACAACCCCGUG GAAGGAGU | 10 |
| NA | VP40-AUG | UCCCAAUCUCAGCUUGUUGAAUUAAUUGU UACUUAAGUCAUUCUUUUUAAAAUUAAUU CACACAAGGUAGUUUGGGUUUAUAUCUAG AACAAAUUUUAAUAUGGCCAGUUCCAGCA AUUACAACA | 11 |
| NA | L-AUG | UCAUUCUCUUCGAUACACGUUAUAUCUUU AGCAAAGUAAUGAAAAAUAGCCUUGUCAUG | 12 |

Sequence Listing Table

| AVI No. | Name | Target Sequences (5'-3') | SEQ ID NO |
|---|---|---|---|
| | | UUAGACGCCAGUUAUCCAUCUUAAGUGAAUCCUUUCUUCAAUAUGCAGCAUCCAACUCAAUAUCCUG | |
| NA | NP-AUG | CACACAAAAACAAGAGAUGAUGAUUUUGUGUAUCAUAUAAAUAAAGAAGAAUAUUAACAUUGAGACUUGUCAGUCUGUUAAUAUUCUUGAAAAGAUGGAUUUACAUAGCUUGUUAGAGU | 13 |
| NA | Str. Ihn 1(-) | CAAAAUCAUCAUCUCUUGUUUUUGUGUGUC | 14 |

Ebola Virus Oligomer Targeting Sequences (5'-3')

| AVI No. | Name | Target Sequences (5'-3') | SEQ ID NO |
|---|---|---|---|
| 305 | Str. Inh. 1 | CGGACACACAAAAGAAAGAAG | 15 |
| 309 | L-AUG | GTAGCCATTAATATCAAGAGG | 16 |
| 538 | L'-AUG | TGGGTATGTTGTGTAGCCAT | 17 |
| 1156 | L-29-AUG | CAAGAGGAAGAATTTCAACTGC | 18 |
| 1157 | L+4-AUG | GTATTGGGTATGTTGTGTAGC | 19 |
| 1158 | L+11-AUG | CGTCTGGGTATTGGGTATGTT | 20 |
| 413 | VP35-AUG | GTTGTCATCTTGTTAGACCAGC | 21 |
| 539 | VP35'-AUG | CCTGCCCTTTGTTCTAGTTG | 22 |
| 565 | VP35-22-AUG | GATGAAGGTTTTAATCTTCATC | 23 |
| 540 | VP35-19-AUG | GTCATCTTGTAGACCAGC | 24 |
| 541 | VP35-16-AUG | GTCATCTTGTTAGACC | 25 |
| 1151 | VP35+2-AUG | CCTGCCCTTTGTTCTAGTTGTC | 26 |
| 534 | NP-AUG | GGACGAGAATCCATACTCGG | 27 |
| 1147 | NP+4-AUG | CAGATTTTCTGAGGACGAGAATC | 28 |
| 1148 | NP+11-AUG | CATCCAGATTTTCTGAGGAC | 29 |
| 1149 | NP+18-AUG | CTCGGCGCCATCCAGATTTTC | 30 |
| 1150 | NP-19-AUG | CATACTCGGAATTTTGTGATTC | 31 |
| 535 | VP40-AUG | GGCAATATAACCCGCCTC | 32 |
| 536 | VP30-AUG | CCATTTAAAAGTTGTCTCC | 33 |
| 537 | VP24-AUG | GCCATGGTTTTTTCTCAGG | 34 |
| 1152 | VP24-28-AUG | CTCAGGTCTTGCTTGGTGTC | 35 |
| 1153 | VP24+4-AUG | TGTATCGTCCCGTAGCTTAGC | 36 |
| 1154 | VP24+10-AUG | GATTGTATCGTCCCGTAGC | 37 |
| 1155 | VP24+19-AUG | GGCGATATTAGATTGTATCGTC | 38 |
| 0165 | VP24-5'trm | TTCAACCTTGAAACCTTGCG | 39 |
| 0164 | VP24(8+)-AUG | GCCA+TGG+T+T+T+T+T+TC+TCAGG | 40 |
| 0166 | VP24-5'trm(6+) | +T+TCAACC+T+TGAAACC+T+TGCG | 41 |
| NA | panVP35 | GATGAAGGTTTTAATCTTCATC | 42 |
| NA | Scrv3 | TTTTTCTTAATCTTCATC | 43 |

Marburg Virus Oligomer Targeting Sequences (5'-3')

| AVI No. | Name | Target Sequences (5'-3') | SEQ ID NO |
|---|---|---|---|
| NA | (-)3'term | GACACACAAAAACAAGAGATG | 44 |
| NA | L-AUG | GCTGCATATTGAAGAAAGG | 45 |
| 0177 | L+7-AUG | CATCAGGATATTGAGTTGGATG | 46 |
| NA | VP35-AUG | GTCCCACATTGTGAAAATTAT | 47 |
| 0178 | VP35+7-AUG | CTTGTTGCATATATGATGAGTC | 48 |
| NA | NP-AUG | GTAAATCCATCTTTTCAAG | 49 |
| 0173 | NP-6-AUG | CAAGCTATGTAAATCCATCTTTTC | 50 |
| 0174 | NP+4-AUG | CCTAACAAGCTATGTAAATC | 51 |
| 0176 | NP-5'SL | TAACAGACTGACAAGTCTCAA | 52 |
| NA | NP-5'UTR | CAATGTTAATATTCTTCTTTA | 53 |
| 0175 | NP-5'UTRb | ATATTCTTCTTTATTTATATGT | 54 |
| NA | VP30-AUG | GTTGCATTTAAATCTTGAATC | 55 |
| NA | VP35-5'UTR | CCTTTAATATTCTTCGATTT | 56 |
| 0179 | VP24+5-AUG | GTTGTAACGCGTTGATAATTCTG | 57 |
| NA | NP-stem loop | CAAGTCTCAATGTCAATGTT | 58 |

Control Oligomers

| AVI No. | Name | Target Sequences (5'-3') | SEQ ID NO |
|---|---|---|---|
| 183 | DSscr | AGTCTCGACTTGCTACCTCA | 59 |
| 542 | Scr | TGTGCTTACTGTTATACTACTC | 60 |

Peptide Conjugates*

| AVI No. | Name | Target Sequences (5'-3') | SEQ ID NO |
|---|---|---|---|
| NA | R9F2C | $NH_2$-RRRRRRRRRFFC-$CO_2H$ | 61 |
| NA | RXR4 | $NH_2$-RXRRXRRXRRXRXB-$CO_2H$ | 62 |
| NA | P008RX8 | $NH_2$-RXRXRXRXRXRXRXRXB-$CO_2H$ | 63 |
| NA | RX4 | $NH_2$-RXRXRXRXB-$CO_2H$ | 64 |
| NA | RXR2 | $NH_2$-RXRRXRXB-$CO_2H$ | 65 |
| NA | RXR3 | $NH_2$-RXRRXRRXRXB-$CO_2H$ | 66 |

*"X" and "B" denote 6-aminohexanoic acid and beta-alanine, respectively.

**SEQ ID NOs:40 and 41 incorporated the cationic linkage (1-piperazino phosphoramidate) as shown in FIG. 2H, at the positions indicated with a "+".

It is claimed:

1. An antiviral composition for treating an Ebola virus infection, comprising:

an antisense morpholino oligomer composed of morpholino subunits linked by phosphorous-containing intersubunit linkages which join a morpholino nitrogen of one subunit to a 5' exocyclic carbon of an adjacent subunit, wherein the oligomer comprises a targeting sequence which forms a heteroduplex with a target sequence within the AUG start site region of Ebola VP35 mRNA, and wherein the antisense oligomer inhibits virus production, wherein the antisense oligomer has at least 12 contiguous bases from a targeting sequence selected from the group consisting of SEQ ID NOS:21-26.

2. The composition of claim 1, wherein the targeting sequence has the sequence of SEQ ID NO:21.

3. The composition of claim 1, wherein the targeting sequence has the sequence of SEQ ID NO:22.

* * * * *

SEQUENCE LISTING

<160> NUMBER OF SEQ ID NOS: 66

<210> SEQ ID NO 1
<211> LENGTH: 125
<212> TYPE: RNA
<213> ORGANISM: Zaire ebolavirus

<400> SEQUENCE: 1
aaugaugaag auuaaaaccu ucaucauccu uacgucaauu gaauucucua gcacucgaag    60
cuuauugucu ucaauguaaa agaaaagcug gucuaacaag augacaacua gaacaaaggg   120
caggg                                                              125

<210> SEQ ID NO 2
<211> LENGTH: 125
<212> TYPE: RNA
<213> ORGANISM: Zaire ebolavirus

<400> SEQUENCE: 2
cguuccaaca aucgagcgca agguuucaag guugaacuga gagugucuag acaacaaaau    60
auugauacuc cagacaccaa gcaagaccug agaaaaaacc auggcuaaag cuacgggacg   120
auaca                                                              125

<210> SEQ ID NO 3
<211> LENGTH: 125
<212> TYPE: RNA
<213> ORGANISM: Zaire ebolavirus

<400> SEQUENCE: 3
agaucugcga accgguagag uuuaguugca accuaacaca cauaaagcau uggucaaaaa    60
gucaauagaa auuuaaacag ugaguggaga caacuuuuaa auggaagcuu cauaugagag   120
aggac                                                              125

<210> SEQ ID NO 4
<211> LENGTH: 125
<212> TYPE: RNA
<213> ORGANISM: Zaire ebolavirus

<400> SEQUENCE: 4
aaaccaaaag ugaugaagau uaagaaaaac cuaccucggc ugagagagug uuuuuucauu    60
aaccuucauc uuguaaacgu ugagcaaaau uguuaaaaau augaggcggg uuauauugcc   120
uacug                                                              125

<210> SEQ ID NO 5
<211> LENGTH: 124
<212> TYPE: RNA
<213> ORGANISM: Zaire ebolavirus

<400> SEQUENCE: 5
guagauuaag aaaaaagccu gaggaagauu aagaaaaacu gcuuauggg ucuuuccgug     60 uuuuagauga agcaguugaa auucuuccuc uugauauuaa auggcuacac aacauaccca   120
auac                                                               124

<210> SEQ ID NO 6
<211> LENGTH: 125
<212> TYPE: RNA
<213> ORGANISM: Zaire ebolavirus -continued

```
<400> SEQUENCE: 6
ugaacacuua ggggauugaa gauucaacaa cccuaaagcu ugggguaaaa cauuggaaau      60
aguuaaaaga caaauugcuc ggaaucacaa aauuccgagu auggauucuc guccucagaa     120
aaucu                                                                 125

<210> SEQ ID NO 7
<211> LENGTH: 30
<212> TYPE: RNA
<213> ORGANISM: Zaire ebolavirus

<400> SEQUENCE: 7
uaaaaauucu ucuuucuuuu uguguguccg                                       30

<210> SEQ ID NO 8
<211> LENGTH: 125
<212> TYPE: RNA
<213> ORGANISM: Lake victoria marburgvirus

<400> SEQUENCE: 8
cuaaaaaucg aagaauauua aagguuuucu uuaauauuca gaaagguuu uuuauucucu       60 ucuuucuuuu ugcaaacaua uugaaauaau aauuuucaca auggggacu caucauauau     120 gcaac                                                                 125

<210> SEQ ID NO 9
<211> LENGTH: 125
<212> TYPE: RNA
<213> ORGANISM: Lake victoria marburgvirus

<400> SEQUENCE: 9
uucauucaaa caccccaaau uuucaaucau acacauaaua accauuuuag uagcguuacc      60
uuucaauaca aucuaggguga uugugaaaag acuuccaaac auggcagaau uaucaacgcg   120
uuaca                                                                 125

<210> SEQ ID NO 10
<211> LENGTH: 124
<212> TYPE: RNA
<213> ORGANISM: Lake victoria marburgvirus

<400> SEQUENCE: 10
gaagaacauu aaguguucuu uguuagaauu auucauccaa guuguuuuga guauacucgc      60
uucaauacaa cuucccuuca uauuugauuc aagauuuaaa augcaacaac cccguggaag    120
gagu                                                                  124

<210> SEQ ID NO 11
<211> LENGTH: 125
<212> TYPE: RNA
<213> ORGANISM: Lake victoria marburgvirus

<400> SEQUENCE: 11
ucccaaucuc agcuuguuga auuaauuguu acuuaaguca uucuuuuuaa aauuaauuca      60
cacaagguag uuugggguuua uaucuagaac aaauuuuaau auggccaguu ccagcaauua   120
caaca                                                                 125

<210> SEQ ID NO 12
<211> LENGTH: 125
<212> TYPE: RNA
```

<213> ORGANISM: Lake victoria marburgvirus

<400> SEQUENCE: 12

```
ucauucucuu cgauacacgu uauaucuuua gcaaaguaau gaaaauagcc uugucauguu      60
agacgccagu uauccaucuu aagugaaucc uuucuucaau augcagcauc caacucaaua     120
uccug                                                                125
```

<210> SEQ ID NO 13
<211> LENGTH: 125
<212> TYPE: RNA
<213> ORGANISM: Lake victoria marburgvirus

<400> SEQUENCE: 13

```
cacacaaaaa caagagauga ugauuuugug uaucauauaa auaaagaaga auauuaacau      60
ugacauugag acuugucagu cuguuaauau ucuugaaaag auggauuuac auagcuuguu     120
agagu                                                                125
```

<210> SEQ ID NO 14
<211> LENGTH: 30
<212> TYPE: RNA
<213> ORGANISM: Lake victoria marburgvirus

<400> SEQUENCE: 14

```
caaaaucauc aucucuuguu uuugugugue                                      30
```

<210> SEQ ID NO 15
<211> LENGTH: 22
<212> TYPE: DNA
<213> ORGANISM: Artificial sequence
<220> FEATURE:
<223> OTHER INFORMATION: Synthetic oligomer

<400> SEQUENCE: 15

```
cggacacaca aaagaaaga ag                                               22
```

<210> SEQ ID NO 16
<211> LENGTH: 22
<212> TYPE: DNA
<213> ORGANISM: Artificial sequence
<220> FEATURE:
<223> OTHER INFORMATION: Synthetic oligomer

<400> SEQUENCE: 16

```
gtagccattt aatatcaaga gg                                              22
```

<210> SEQ ID NO 17
<211> LENGTH: 20
<212> TYPE: DNA
<213> ORGANISM: Artificial sequence
<220> FEATURE:
<223> OTHER INFORMATION: Synthetic oligomer

<400> SEQUENCE: 17

```
tgggtatgtt gtgtagccat                                                 20
```

<210> SEQ ID NO 18
<211> LENGTH: 22
<212> TYPE: DNA
<213> ORGANISM: Artificial sequence
<220> FEATURE:
<223> OTHER INFORMATION: Synthetic oligomer

<400> SEQUENCE: 18
```

-continued caagaggaag aatttcaact gc    22

<210> SEQ ID NO 19
<211> LENGTH: 21
<212> TYPE: DNA
<213> ORGANISM: Artificial sequence
<220> FEATURE:
<223> OTHER INFORMATION: Synthetic oligomer

<400> SEQUENCE: 19
gtattgggta tgttgtgtag c    21

<210> SEQ ID NO 20
<211> LENGTH: 21
<212> TYPE: DNA
<213> ORGANISM: Artificial sequence
<220> FEATURE:
<223> OTHER INFORMATION: Synthetic oligomer

<400> SEQUENCE: 20
cgtctgggta ttgggtatgt t    21

<210> SEQ ID NO 21
<211> LENGTH: 22
<212> TYPE: DNA
<213> ORGANISM: Artificial sequence
<220> FEATURE:
<223> OTHER INFORMATION: Synthetic oligomer

<400> SEQUENCE: 21
gttgtcatct tgttagacca gc    22

<210> SEQ ID NO 22
<211> LENGTH: 20
<212> TYPE: DNA
<213> ORGANISM: Artificial sequence
<220> FEATURE:
<223> OTHER INFORMATION: Synthetic oligomer

<400> SEQUENCE: 22
cctgcccttt gttctagttg    20

<210> SEQ ID NO 23
<211> LENGTH: 22
<212> TYPE: DNA
<213> ORGANISM: Artificial sequence
<220> FEATURE:
<223> OTHER INFORMATION: Synthetic oligomer

<400> SEQUENCE: 23
gatgaaggtt ttaatcttca tc    22

<210> SEQ ID NO 24
<211> LENGTH: 18
<212> TYPE: DNA
<213> ORGANISM: Artificial sequence
<220> FEATURE:
<223> OTHER INFORMATION: Synthetic oligomer

<400> SEQUENCE: 24
gtcatcttgt agaccagc    18

<210> SEQ ID NO 25
<211> LENGTH: 16
<212> TYPE: DNA

```
<213> ORGANISM: Artificial sequence
<220> FEATURE:
<223> OTHER INFORMATION: Synthetic oligomer

<400> SEQUENCE: 25
gtcatcttgt tagacc                                                   16

<210> SEQ ID NO 26
<211> LENGTH: 22
<212> TYPE: DNA
<213> ORGANISM: Artificial sequence
<220> FEATURE:
<223> OTHER INFORMATION: Synthetic oligomer

<400> SEQUENCE: 26
cctgcccttt gttctagttg tc                                            22

<210> SEQ ID NO 27
<211> LENGTH: 20
<212> TYPE: DNA
<213> ORGANISM: Artificial sequence
<220> FEATURE:
<223> OTHER INFORMATION: Synthetic oligomer

<400> SEQUENCE: 27
ggacgagaat ccatactcgg                                               20

<210> SEQ ID NO 28
<211> LENGTH: 23
<212> TYPE: DNA
<213> ORGANISM: Artificial sequence
<220> FEATURE:
<223> OTHER INFORMATION: Synthetic oligomer

<400> SEQUENCE: 28
cagattttct gaggacgaga atc                                           23

<210> SEQ ID NO 29
<211> LENGTH: 20
<212> TYPE: DNA
<213> ORGANISM: Artificial sequence
<220> FEATURE:
<223> OTHER INFORMATION: Synthetic oligomer

<400> SEQUENCE: 29
catccagatt ttctgaggac                                               20

<210> SEQ ID NO 30
<211> LENGTH: 21
<212> TYPE: DNA
<213> ORGANISM: Artificial sequence
<220> FEATURE:
<223> OTHER INFORMATION: Synthetic oligomer

<400> SEQUENCE: 30
ctcggcgcca tccagatttt c                                             21

<210> SEQ ID NO 31
<211> LENGTH: 22
<212> TYPE: DNA
<213> ORGANISM: Artificial sequence
<220> FEATURE:
<223> OTHER INFORMATION: Synthetic oligomer

<400> SEQUENCE: 31
catactcgga attttgtgat tc                                            22
```

<210> SEQ ID NO 32
<211> LENGTH: 18
<212> TYPE: DNA
<213> ORGANISM: Artificial sequence
<220> FEATURE:
<223> OTHER INFORMATION: Synthetic oligomer

<400> SEQUENCE: 32
ggcaatataa cccgcctc                                                 18

<210> SEQ ID NO 33
<211> LENGTH: 19
<212> TYPE: DNA
<213> ORGANISM: Artificial sequence
<220> FEATURE:
<223> OTHER INFORMATION: Synthetic oligomer

<400> SEQUENCE: 33
ccatttaaaa gttgtctcc                                                19

<210> SEQ ID NO 34
<211> LENGTH: 19
<212> TYPE: DNA
<213> ORGANISM: Artificial sequence
<220> FEATURE:
<223> OTHER INFORMATION: Synthetic oligomer

<400> SEQUENCE: 34
gccatggttt tttctcagg                                                19

<210> SEQ ID NO 35
<211> LENGTH: 20
<212> TYPE: DNA
<213> ORGANISM: Artificial sequence
<220> FEATURE:
<223> OTHER INFORMATION: Synthetic oligomer

<400> SEQUENCE: 35
ctcaggtctt gcttggtgtc                                               20

<210> SEQ ID NO 36
<211> LENGTH: 22
<212> TYPE: DNA
<213> ORGANISM: Artificial sequence
<220> FEATURE:
<223> OTHER INFORMATION: Synthetic oligomer

<400> SEQUENCE: 36
tgtatcgtcc cgtagcttta gc                                            22

<210> SEQ ID NO 37
<211> LENGTH: 19
<212> TYPE: DNA
<213> ORGANISM: Artificial sequence
<220> FEATURE:
<223> OTHER INFORMATION: Synthetic oligomer

<400> SEQUENCE: 37
gattgtatcg tcccgtagc                                                19

<210> SEQ ID NO 38
<211> LENGTH: 22
<212> TYPE: DNA
<213> ORGANISM: Artificial sequence
<220> FEATURE:

```
<223> OTHER INFORMATION: Synthetic oligomer

<400> SEQUENCE: 38
ggcgatatta gattgtatcg tc                                              22

<210> SEQ ID NO 39
<211> LENGTH: 20
<212> TYPE: DNA
<213> ORGANISM: Artificial sequence
<220> FEATURE:
<223> OTHER INFORMATION: Synthetic oligomer

<400> SEQUENCE: 39
ttcaaccttg aaaccttgcg                                                 20

<210> SEQ ID NO 40
<211> LENGTH: 19
<212> TYPE: DNA
<213> ORGANISM: Artificial sequence
<220> FEATURE:
<223> OTHER INFORMATION: Synthetic oligomer

<400> SEQUENCE: 40
gccatggttt tttctcagg                                                  19

<210> SEQ ID NO 41
<211> LENGTH: 20
<212> TYPE: DNA
<213> ORGANISM: Artificial sequence
<220> FEATURE:
<223> OTHER INFORMATION: Synthetic oligomer

<400> SEQUENCE: 41
ttcaaccttg aaaccttgcg                                                 20

<210> SEQ ID NO 42
<211> LENGTH: 22
<212> TYPE: DNA
<213> ORGANISM: Artificial sequence
<220> FEATURE:
<223> OTHER INFORMATION: Synthetic oligomer

<400> SEQUENCE: 42
gatgaaggtt ttaatcttca tc                                              22

<210> SEQ ID NO 43
<211> LENGTH: 18
<212> TYPE: DNA
<213> ORGANISM: Artificial sequence
<220> FEATURE:
<223> OTHER INFORMATION: Synthetic oligomer

<400> SEQUENCE: 43
tttttcttaa tcttcatc                                                   18

<210> SEQ ID NO 44
<211> LENGTH: 21
<212> TYPE: DNA
<213> ORGANISM: Artificial sequence
<220> FEATURE:
<223> OTHER INFORMATION: Synthetic oligomer

<400> SEQUENCE: 44
gacacacaaa aacaagagat g                                               21
```

```
<210> SEQ ID NO 45
<211> LENGTH: 19
<212> TYPE: DNA
<213> ORGANISM: Artificial sequence
<220> FEATURE:
<223> OTHER INFORMATION: Synthetic oligomer

<400> SEQUENCE: 45
gctgcatatt gaagaaagg                                                  19

<210> SEQ ID NO 46
<211> LENGTH: 22
<212> TYPE: DNA
<213> ORGANISM: Artificial sequence
<220> FEATURE:
<223> OTHER INFORMATION: Synthetic oligomer

<400> SEQUENCE: 46
catcaggata ttgagttgga tg                                              22

<210> SEQ ID NO 47
<211> LENGTH: 21
<212> TYPE: DNA
<213> ORGANISM: Artificial sequence
<220> FEATURE:
<223> OTHER INFORMATION: Synthetic oligomer

<400> SEQUENCE: 47
gtcccacatt gtgaaaatta t                                               21

<210> SEQ ID NO 48
<211> LENGTH: 22
<212> TYPE: DNA
<213> ORGANISM: Artificial sequence
<220> FEATURE:
<223> OTHER INFORMATION: Synthetic oligomer

<400> SEQUENCE: 48
cttgttgcat atatgatgag tc                                              22

<210> SEQ ID NO 49
<211> LENGTH: 19
<212> TYPE: DNA
<213> ORGANISM: Artificial sequence
<220> FEATURE:
<223> OTHER INFORMATION: Synthetic oligomer

<400> SEQUENCE: 49
gtaaatccat cttttcaag                                                  19

<210> SEQ ID NO 50
<211> LENGTH: 24
<212> TYPE: DNA
<213> ORGANISM: Artificial sequence
<220> FEATURE:
<223> OTHER INFORMATION: Synthetic oligomer

<400> SEQUENCE: 50
caagctatgt aaatccatct tttc                                            24

<210> SEQ ID NO 51
<211> LENGTH: 20
<212> TYPE: DNA
<213> ORGANISM: Artificial sequence
<220> FEATURE:
<223> OTHER INFORMATION: Synthetic oligomer
```

<400> SEQUENCE: 51
cctaacaagc tatgtaaatc                                              20

<210> SEQ ID NO 52
<211> LENGTH: 21
<212> TYPE: DNA
<213> ORGANISM: Artificial sequence
<220> FEATURE:
<223> OTHER INFORMATION: Synthetic oligomer

<400> SEQUENCE: 52
taacagactg acaagtctca a                                            21

<210> SEQ ID NO 53
<211> LENGTH: 21
<212> TYPE: DNA
<213> ORGANISM: Artificial sequence
<220> FEATURE:
<223> OTHER INFORMATION: Synthetic oligomer

<400> SEQUENCE: 53
caatgttaat attcttcttt a                                            21

<210> SEQ ID NO 54
<211> LENGTH: 22
<212> TYPE: DNA
<213> ORGANISM: Artificial sequence
<220> FEATURE:
<223> OTHER INFORMATION: Synthetic oligomer

<400> SEQUENCE: 54
atattcttct ttatttatat gt                                           22

<210> SEQ ID NO 55
<211> LENGTH: 22
<212> TYPE: DNA
<213> ORGANISM: Artificial sequence
<220> FEATURE:
<223> OTHER INFORMATION: Synthetic oligomer

<400> SEQUENCE: 55
gttgcatttt aaatcttgaa tc                                           22

<210> SEQ ID NO 56
<211> LENGTH: 20
<212> TYPE: DNA
<213> ORGANISM: Artificial sequence
<220> FEATURE:
<223> OTHER INFORMATION: Synthetic oligomer

<400> SEQUENCE: 56
cctttaatat tcttcgattt                                              20

<210> SEQ ID NO 57
<211> LENGTH: 23
<212> TYPE: DNA
<213> ORGANISM: Artificial sequence
<220> FEATURE:
<223> OTHER INFORMATION: Synthetic oligomer

<400> SEQUENCE: 57
gttgtaacgc gttgataatt ctg                                          23

<210> SEQ ID NO 58
<211> LENGTH: 20

<212> TYPE: DNA
<213> ORGANISM: Artificial sequence
<220> FEATURE:
<223> OTHER INFORMATION: Synthetic oligomer

<400> SEQUENCE: 58
caagtctcaa tgtcaatgtt                                           20

<210> SEQ ID NO 59
<211> LENGTH: 20
<212> TYPE: DNA
<213> ORGANISM: Artificial sequence
<220> FEATURE:
<223> OTHER INFORMATION: Synthetic oligomer

<400> SEQUENCE: 59
agtctcgact tgctacctca                                           20

<210> SEQ ID NO 60
<211> LENGTH: 22
<212> TYPE: DNA
<213> ORGANISM: Artificial sequence
<220> FEATURE:
<223> OTHER INFORMATION: Synthetic oligomer

<400> SEQUENCE: 60
tgtgcttact gttatactac tc                                        22

<210> SEQ ID NO 61
<211> LENGTH: 12
<212> TYPE: PRT
<213> ORGANISM: Artificial sequence
<220> FEATURE:
<223> OTHER INFORMATION: Synthetic arginine-rich peptide

<400> SEQUENCE: 61

Arg Arg Arg Arg Arg Arg Arg Arg Arg Phe Phe Cys
1               5                   10

<210> SEQ ID NO 62
<211> LENGTH: 14
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(13)
<223> OTHER INFORMATION: Xaa=6-aminohexanoic acid
<220> FEATURE:
<221> NAME/KEY: VARIANT
<222> LOCATION: (14)..(14)
<223> OTHER INFORMATION: Xaa=beta-alanine

<400> SEQUENCE: 62

Arg Xaa Arg Arg Xaa Arg Arg Xaa Arg Arg Xaa Arg Xaa Xaa
1               5                   10

<210> SEQ ID NO 63
<211> LENGTH: 17
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(16)
<223> OTHER INFORMATION: Xaa=6-aminohexanoic acid
<220> FEATURE:

-continued

```
<221> NAME/KEY: VARIANT
<222> LOCATION: (17)..(17)
<223> OTHER INFORMATION: Xaa=beta-alanine

<400> SEQUENCE: 63

Arg Xaa Arg Xaa Arg Xaa Arg Xaa Arg Xaa Arg Xaa Arg Xaa Arg Xaa
1               5                   10                  15
Xaa

<210> SEQ ID NO 64
<211> LENGTH: 9
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(8)
<223> OTHER INFORMATION: Xaa=6-aminohexanoic acid
<220> FEATURE:
<221> NAME/KEY: VARIANT
<222> LOCATION: (9)..(9)
<223> OTHER INFORMATION: Xaa=beta-alanine

<400> SEQUENCE: 64

Arg Xaa Arg Xaa Arg Xaa Arg Xaa Xaa
1               5

<210> SEQ ID NO 65
<211> LENGTH: 8
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(7)
<223> OTHER INFORMATION: Xaa=6-aminohexanoic acid
<220> FEATURE:
<221> NAME/KEY: VARIANT
<222> LOCATION: (8)..(8)
<223> OTHER INFORMATION: Xaa=beta-alanine

<400> SEQUENCE: 65

Arg Xaa Arg Arg Xaa Arg Xaa Xaa
1               5

<210> SEQ ID NO 66
<211> LENGTH: 11
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(10)
<223> OTHER INFORMATION: Xaa=6-aminohexanoic acid
<220> FEATURE:
<221> NAME/KEY: VARIANT
<222> LOCATION: (11)..(11)
<223> OTHER INFORMATION: Xaa=beta-alanine

<400> SEQUENCE: 66

Arg Xaa Arg Arg Xaa Arg Arg Xaa Arg Xaa Xaa
1               5                   10
```